(12) United States Patent
Takahashi et al.

(10) Patent No.: US 8,709,308 B2
(45) Date of Patent: Apr. 29, 2014

(54) CHROMENE COMPOUND

(75) Inventors: Toshiaki Takahashi, Shunan (JP); Junji Takenaka, Shunan (JP); Junji Momoda, Shunan (JP); Kazuhiro Teranishi, Shunan (JP); Mitsuyoshi Sando, Shunan (JP); Shinobu Izumi, Shunan (JP)

(73) Assignee: Tokuyama Corporation, Shunan-Shi (JP)

( * ) Notice: Subject to any disclaimer, the term of this patent is extended or adjusted under 35 U.S.C. 154(b) by 0 days.

(21) Appl. No.: 13/982,132

(22) PCT Filed: Jan. 26, 2012

(86) PCT No.: PCT/JP2012/052326
§ 371 (c)(1),
(2), (4) Date: Oct. 15, 2013

(87) PCT Pub. No.: WO2012/102410
PCT Pub. Date: Aug. 2, 2012

(65) Prior Publication Data
US 2014/0034884 A1 Feb. 6, 2014

(30) Foreign Application Priority Data

Jan. 28, 2011 (JP) ................................. 2011-016936
Jan. 31, 2011 (JP) ................................. 2011-017703

(51) Int. Cl.
| | | |
|---|---|---|
| G02B 5/23 | (2006.01) |
| F21V 9/00 | (2006.01) |
| G02B 5/02 | (2006.01) |
| G02C 7/10 | (2006.01) |
| G02F 1/361 | (2006.01) |
| G03B 11/00 | (2006.01) |
| G02F 1/03 | (2006.01) |
| G02F 1/07 | (2006.01) |

(52) U.S. Cl.
USPC ............. 252/586; 252/582; 359/241; 544/79; 544/129; 544/141; 544/143; 544/150; 544/154; 546/15; 548/407; 549/330; 549/382; 549/406; 549/502; 564/114; 564/426; 568/325; 568/633

(58) Field of Classification Search
USPC ............. 252/582, 586; 359/241; 544/79, 129, 544/141, 143, 150, 154; 546/15; 548/407; 549/330, 382, 406, 502; 564/114, 426; 568/325, 633
See application file for complete search history.

(56) References Cited

U.S. PATENT DOCUMENTS

| | | | |
|---|---|---|---|
| 6,146,554 A | 11/2000 | Melzig et al. |
| 6,296,785 B1 | 10/2001 | Nelson et al. |
| 6,723,859 B2 | 4/2004 | Kawabata et al. |
| 7,166,357 B2 | 1/2007 | Kumar et al. |
| 7,517,982 B2 | 4/2009 | Walters et al. |
| 7,521,004 B2 | 4/2009 | Momoda et al. |
| 7,556,751 B2 | 7/2009 | Chopra et al. |
| 8,147,726 B2 | 4/2012 | Kasai et al. |
| 8,308,996 B2 | 11/2012 | Takahashi et al. |
| 2003/0096117 A1 | 5/2003 | Kawabata et al. |
| 2004/0185255 A1 | 9/2004 | Walters et al. |
| 2004/0185268 A1 | 9/2004 | Kumar et al. |
| 2006/0228557 A1 | 10/2006 | Kim et al. |
| 2007/0138449 A1 | 6/2007 | Chopra et al. |
| 2007/0215844 A1 | 9/2007 | Momoda et al. |
| 2008/0054942 A1 | 3/2008 | Drapkin et al. |
| 2008/0103301 A1 | 5/2008 | Chopra et al. |
| 2009/0032782 A1 | 2/2009 | Kim et al. |
| 2009/0309076 A1 | 12/2009 | He et al. |

(Continued)

FOREIGN PATENT DOCUMENTS

| | | |
|---|---|---|
| JP | 2008-535971 A | 9/2008 |
| JP | 2009-521542 A | 6/2009 |

(Continued)

OTHER PUBLICATIONS

International Search Report issued in PCT/JP2012/052326, mailed on Mar. 19, 2012.

(Continued)

*Primary Examiner* — Bijan Ahvazi
(74) *Attorney, Agent, or Firm* — Birch, Stewart, Kolasch & Birch, LLP

(57) ABSTRACT

The chromene compound is represented by the following formula (I),

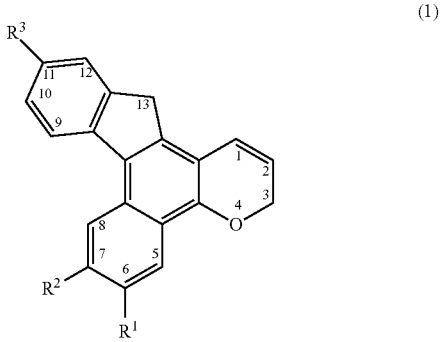

(1)

wherein $R^3$ at the 11-position is a sulfur-containing substituent selected from the group consisting of thiol group, alkylthio group, alkoxyalkylthio group, haloalkylthio group, cycloalkylthio group, arylthio group, heteroarylthio group, sulfonyl group and sulfinyl group, $R^1$ and $R^2$ at the 6-position and the 7-position are a combination of an aryl group or a heteroaryl group and an electron donating group having a Hammett constant $\sigma_p$ of −0.1 or less, or $R^1$ and/or $R^2$ is sulfur-containing substituent selected from thiol group, alkylthio group, alkoxyalkylthio group, haloalkylthio group, cycloalkylthio group, arylthio group and heteroarylthio group.

19 Claims, No Drawings

(56) References Cited

U.S. PATENT DOCUMENTS

2012/0121934 A1   5/2012   Takahashi et al.
2012/0138876 A1   6/2012   Kasai et al.
2012/0270071 A1   10/2012  Takahashi et al.

FOREIGN PATENT DOCUMENTS

| WO | WO 99/15518 A1 | 4/1999 |
| WO | WO 00/35902 A1 | 6/2000 |
| WO | WO 01/19813 A1 | 3/2001 |
| WO | WO 01/60811 A1 | 8/2001 |
| WO | WO 2004/085569 A2 | 10/2004 |
| WO | WO 2005/028465 A1 | 3/2005 |
| WO | WO 2005/090327 A1 | 9/2005 |
| WO | WO 2006/110221 A1 | 10/2006 |
| WO | WO 2008/054942 A2 | 5/2008 |
| WO | WO 2009/136668 A1 | 11/2009 |
| WO | WO 2011/010744 A1 | 1/2011 |
| WO | WO 2011/016582 A1 | 2/2011 |

OTHER PUBLICATIONS

International Preliminary Examination Report dated Aug. 8, 2013 in PCT/JP2012/052326 (Forms PCT/IB/338, PCT/IB/373 and PCT/ISA/237).

CHROMENE COMPOUND

TECHNICAL FIELD

The present invention relates to a photochromic chromene compound, and use and an intermediate thereof. More specifically, it relates to a chromene compound which is useful as a photochromic compound for photochromic spectacle lenses, and use and an intermediate thereof.

BACKGROUND ART

Photochromism is the reversible function of a certain compound that it changes its color swiftly upon exposure to light including ultraviolet light such as sunlight or light from a mercury lamp and returns to its original color when it is put in the dark by stopping its exposure to light. A compound having this property is called "photochromic compound" and used as a material for photochromic plastic lenses.

For the photochromic compound used for this purpose, the following properties are required: (I) the degree of coloration at a visible light range before ultraviolet light is applied (to be referred to as "initial coloration" hereinafter) should be low, (II) the degree of coloration upon exposure to ultraviolet light (to be referred to as "color optical density" hereinafter) should be high, (III) the speed from the time when the application of ultraviolet light is started to the time when the color optical density reaches saturation (to be referred to as "color development sensitivity" hereinafter) should be high; (IV) the speed from the stoppage of the application of ultraviolet light to the time when the compound returns to its original state (to be referred to as "fading speed" hereinafter) should be high, (V) the repeat durability of this reversible function should be high, and (VI) the solubility in a monomer composition which will become a host material after curing of the photochromic compound should be high so that its dispersibility in the host material in use becomes high.

As the photochromic compound which can satisfy these requirements, there are known chromene compounds having an indeno(2,1-f)naphtho(1,2-b)pyran structure as the basic skeleton (refer to a pamphlet of International Laid-Open WO99/15518 and a pamphlet of International Laid-Open WO2001/60811).

It is preferred that a photochromic plastic lens comprising the photochromic compound should develop a color of a neutral tint such as gray or brown. A color of a neutral tint is obtained by mixing together several different kinds of photochromic compounds which develop different colors, for example, a yellow to red photochromic compound (yellow compound) having a maximum absorption at 430 to 530 nm and a purple to blue photochromic compound (blue compound) having a maximum absorption at 550 to 650 nm.

However, when color control is carried out by this method, various problems occur due to the difference in photochromic properties between the compounds which have been mixed together. For example, when the repeat durability of the yellow compound is lower than that of the blue compound and the photochromic plastic lens is used for a long time, there occurs a problem that the developed color gradually changes to a color of a strong blue tint.

Further, when the color development sensitivity and fading speed of the yellow compound are lower than those of the blue compound, there arises a problem that color during development has a strong blue tint and color during fading has a strong yellow tint.

It is considered that this problem can be solved by using a single compound which has two or more absorption maximums at the time of exposure and develops a color of a neutral tint (double peak compound). It is known that the yellow compound is generally inferior to the blue compound in durability. Therefore, a compound having higher yellow color optical density (having a maximum absorption wavelength at 430 to 530 nm) than blue color optical density (having a maximum absorption wavelength at 550 to 650 nm) is desired as the double peak compound (the ratio of the yellow color optical density to the blue color optical density in the double peak compound may be referred to as "double peak characteristic" hereinafter). When the ratio of the yellow color optical density to the blue color optical density is 0.8 or more to less than 1.1, a good gray color is obtained and when the ratio is 1.1 to 2.0, a good brown color is obtained. Therefore, when the double peak characteristic is less than 0.8, a blue or purple tint becomes strong and when the double peak characteristic is 2.0 or more, a yellow or orange tint becomes strong.

As the photochromic compound having two or more absorption maximums at the time of color development (double peak compound), there are known compounds represented by the following formulas (A) to (G) and having an indeno(2,1-f)naphtho(1,2-b)pyran structure as the basic skeleton.

However, these compounds have room for the improvement of the following points. That is, a chromene compound represented by the following formula (A) (refer to a pamphlet of International Laid-Open WO01/19813) has low color development sensitivity, low fading speed and low repeat durability though its double peak characteristic is high.

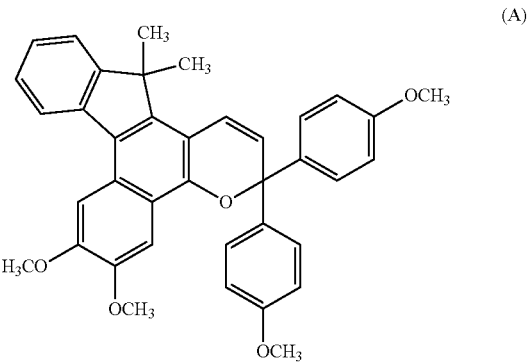 [SMILES: COc1ccc(C2(c3ccc(OC)cc3)C=Cc3c4c(c5cc(OC)c(OC)cc5c3O2)-c2ccccc2C4(C)C)cc1]

(A)

A chromene compound represented by the following formula (B) (refer to a pamphlet of International Laid-Open WO05/028465) has strong initial coloration as the end of its absorption spectrum (to be referred to as "absorption end" hereinafter) goes beyond 420 nm into the visible range though it has excellent double peak characteristic and practical levels of color optical density and fading speed. Although the absorption end is existent at a long wavelength range, as will be described hereinafter, it has low color development sensitivity. Therefore, this chromene compound has room for the improvement of this point as well.

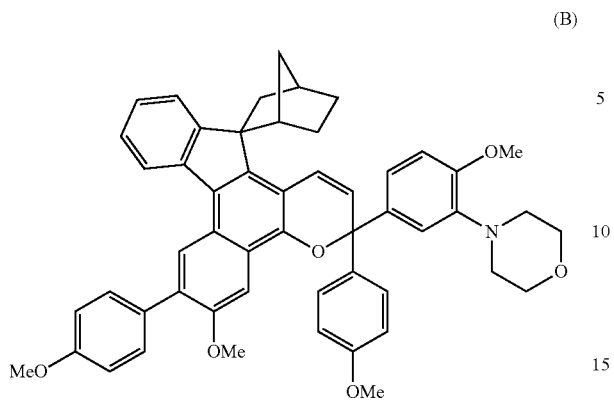

(B)

A chromene compound represented by the following formula (C) (refer to a pamphlet of International Laid-Open WO08/054,942) has low color optical density though it has a practical level of fading speed.

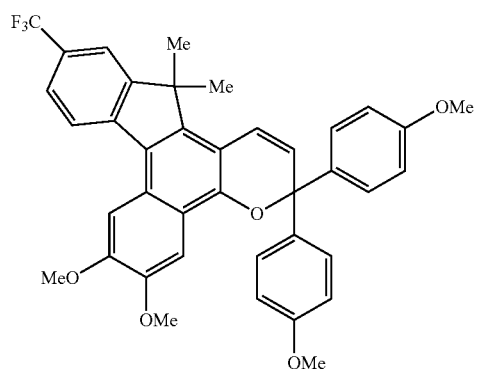

(C)

A chromene compound represented by the following formula (D) (refer to a pamphlet of International Laid-Open WO06/110221) has low color optical density though it has a practical level of fading speed.

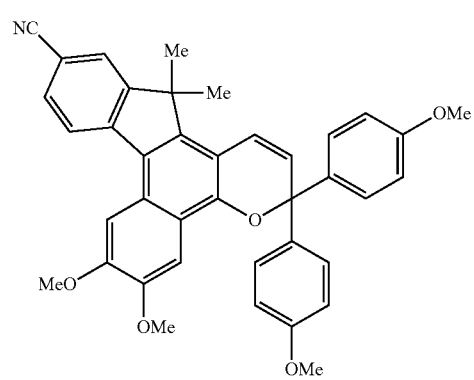

(D)

A chromene compound represented by the following formula (E) (refer to a pamphlet of International Laid-Open WO05/028465) has low double peak characteristic with a smaller absorption at 430 to 530 nm than an absorption at 550 to 650 nm as well as low durability.

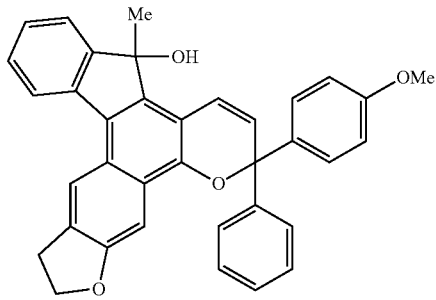

(E)

A chromene compound represented by the following formula (F) which has a trifluoromethylsulfonyloxy group at the 7-position is disclosed by US2009/0309076A1. However, this compound has low double peak characteristic with a smaller absorption at 430 to 530 nm than an absorption at 550 to 650 nm.

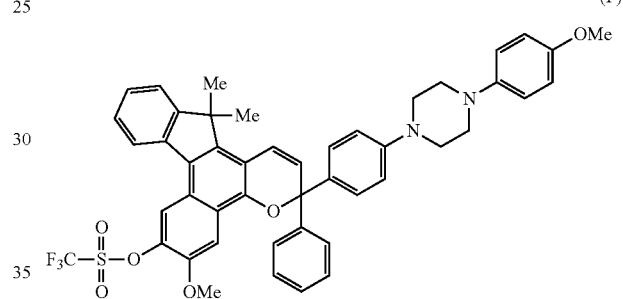

(F)

Further, a compound having a specific substituent at the 11-position is disclosed by a pamphlet of International Laid-Open WO05/090327). Stated more specifically, a chromene compound represented by the following formula (G) is disclosed.

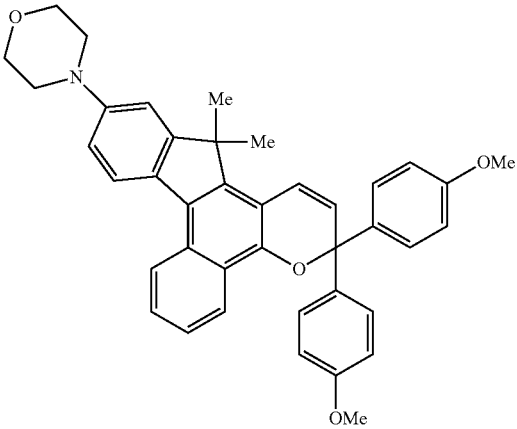

(G)

However, this compound has low double peak characteristic with a smaller absorption at 430 to 530 nm than an absorption at 550 to 650 nm. Also, since its fading speed is very low, it has room for the improvement of this point as well.

Further, in recent years, a photochromic compound which develops a color even inside a car has been desired, and the further improvement of color development sensitivity has been desired.

DISCLOSURE OF THE INVENTION

It is therefore an object of the present invention to provide a chromene compound which develops a color of a neutral tint, has little initial coloration, high double peak characteristic and high color development sensitivity, rarely experiences the reduction of color optical density though it has high fading speed, is excellent in the durability of photochromic properties and can dissolve in a monomer composition which becomes a substrate for optical articles in a high concentration.

It is another object of the present invention to provide a novel naphthol compound for the manufacture of the chromene compound of the present invention.

It is known that a compound having substituents having high electron donating ability bonded to the 6-position and 7-position of an indeno(2,1-f)naphtho(1,2-b)pyran structure exhibits high double peak characteristic. The substituents having high electron donating ability as used herein are substituents bonded to the 6-position and the 7-position via an oxygen atom or a nitrogen atom, respectively. Although the above compound has high double peak characteristic, it has defects such as low fading speed, strong color development by heat at room temperature under no exposure (this color development will be referred to as "initial coloration by thermochromism" hereinafter) and low durability. Particularly when the electron donating abilities of the 6-position and 7-position substituents are further enhanced, the above defects become more marked. It is also known that when an electron suction group is introduced into the 11-position of the indeno(2,1-f)naphtho(1,2-b)pyran structure, the fading speed becomes high but the color optical density lowers. Conversely, when a substituent having high electron donating ability such as an alkoxy group or an amino group is introduced into the 11-position of the above structure, the absorption end of the compound becomes existent at a long wavelength range and the color development sensitivity improves but the fading speed greatly lowers.

Then, the inventors of the present invention conducted intensive studies to solve the above problems and found that when specific substituents are introduced into the 6 position and/or the 7-position and a sulfur-containing substituent is introduced into the 11-position of the indeno(2,1-f)naphtho (1,2-b)pyran structure, a compound which has high double peak characteristic and high fading speed though its color development sensitivity is improved, rarely experiences the reduction of color optical density and has little initial coloration by thermochromism is obtained. The present invention was accomplished based on this finding. Further, since the absorption end of the above compound is existent at a suitable range (not a too short wavelength range and not the visible range), the compound has high color development sensitivity and little initial coloration due to its absorption end. Therefore, a photochromic compound which satisfies all the requirements for a photochromic plastic lens material can be provided, thereby accomplishing the present invention. As for the specific substituents introduced into the 6-position and/or the 7-position, the substituents for the 6-position and the 7-position are a combination of any one of an aryl group and a heteroaryl group and an electron donating substituent having a Hammett constant $\sigma_p$ of −0.1 or less, or any one or both of the 6-position substituent and the 7-position substituent are sulfur-containing substituents containing a sulfur atom. The Hammett constant $\sigma_p$ is defined based on the Hammett equation that quantifies the electric effect of a substituent bonded to an π electron system on the basis of the dissociation constant Ka of p-substituted benzoic acid. A substituent having a $\sigma_p$ of 0 is a hydrogen atom, and a substituent having a $\sigma_p$ of less than 0 is a substituent having higher electron donating ability than a hydrogen atom.

The present invention is a chromene compound having a skeleton represented by the following formula (1).

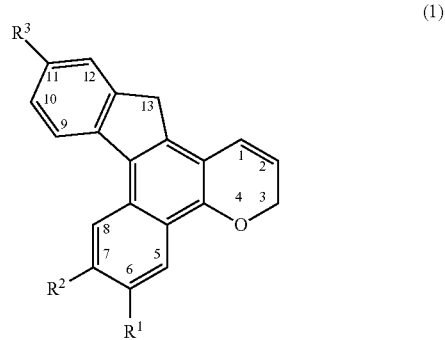

(1)

In the above formula, $R^3$ is a second sulfur-containing substituent selected from the group consisting of thiol group, alkylthio group, alkoxyalkylthio group, haloalkylthio group, cycloalkylthio group, arylthio group, heteroarylthio group, alkylsulfonyl group, alkoxyalkylsulfonyl group, haloalkylsulfonyl group cycloalkylsulfonyl group, arylsulfonyl group, heteroarylsulfonyl group, hydroxysulfonyl group, alkylsulfinyl group, alkoxyalkylsulfinyl group, haloalkylsulfinyl group, cycloalkylsulfinyl group, arylsulfinyl group, heteroarylsulfinyl group and hydroxysulfinyl group, and a combination of $R^1$ and $R^2$ is selected from the following (i) to (v).

(i) $R^1$ is an aryl group or a heteroaryl group, and $R^2$ is an electron donating group having a Hammett constant $\sigma_p$ of −0.1 or less.

(ii) $R^1$ is an electron donating group having a Hammett constant $\sigma_p$ of −0.1 or less, and $R^2$ is an aryl group or a heteroaryl group.

(iii) $R^1$ and $R^2$ are each a first sulfur-containing substituent selected from the group consisting of thiol group, alkylthio group, alkoxyalkylthio group, haloalkylthio group, cycloalkylthio group, arylthio group and heteroarylthio group.

(iv) $R^1$ is the above first sulfur-containing substituent, and $R^2$ is a hydrogen atom, hydroxyl group, alkyl group, haloalkyl group, cycloalkyl group, alkoxy group, amino group, heterocyclic group having a ring member nitrogen atom and bonded to the 7-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group.

(v) $R^1$ is a hydrogen atom, hydroxyl group, alkyl group, haloalkyl group, cycloalkyl group, alkoxy group, amino group, aliphatic heterocyclic group having a ring member nitrogen atom and bonded to the 6-position carbon atom via the nitrogen atom, cyano group, nitro group, formyl group, hydroxycarbonyl group, alkylcarbonyl group, alkoxycarbonyl group, halogen atom, aralkyl group, aralkoxy group or aryloxy group, and $R^2$ is the above first sulfur-containing substituent.

Since these chromene compounds have a double peak characteristic (($A_y/A_B$) which will be described in detail hereinafter) of 0.8 to 2.0, they assume a good color of a neutral tint.

Secondly, the present invention is a photochromic curable composition which comprises the above chromene compound of the present invention and polymerizable monomers.

Thirdly, the present invention is a photochromic optical article having a polymer molded product containing the chromene compound of the present invention dispersed therein as a constituent member.

In the fourth place, the present invention is an optical article having an optical substrate all or part of at least one surface of which is covered with a polymer film containing the chromene compound of the present invention dispersed therein as a constituent member.

In the fifth place, the present invention is a naphthol compound which is a raw material compound for the manufacture of the chromene compound of the present invention.

BEST MODE FOR CARRYING OUT THE INVENTION

The chromene compound of the present invention has an indeno(2,1-f)naphtho(1,2-b)pyran structure represented by the above formula (1) as the basic skeleton. When specific substituents are introduced into the carbon atoms at the 6-position and/or 7-position and 11-position of the basic skeleton, respectively, the chromene compound of the present invention can develop a deep or strong color of a neutral tint by itself while retaining its excellent photochromic properties. As one of the specific substituents, $R^3$ is a second sulfur-containing substituent selected from the group consisting of thiol group, alkylthio group, alkoxyalkylthio group, haloalkylthio group, cycloalkylthio group, arylthio group, heteroarylthio group, alkylsulfonyl group, alkoxyalkylsulfonyl group, haloalkylsulfonyl group cycloalkylsulfonyl group, arylsulfonyl group, heteroarylsulfonyl group, hydroxysulfonyl group, alkylsulfinyl group, alkoxyalkylsulfinyl group, haloalkylsulfinyl group, cycloalkylsulfinyl group, arylsulfinyl group, heteroarylsulfinyl group and hydroxysulfinyl group. As $R^1$ and $R^2$, the substituent at the 6-position is an aryl group or a heteroaryl group and the substituent at the 7-position is an electron donating group having a Hammett constant $\sigma_p$ of −0.1 or less, the substituent at the 6-position is an electron donating group having a Hammett constant $\sigma_p$ of −0.1 or less and the substituent at the 7-position is an aryl group or a heteroaryl group, or at least one of $R^1$ and $R^2$ is a first sulfur-containing substituent selected from the group consisting of thiol group, alkylthio group, alkoxyalkylthio group, haloalkylthio group, cycloalkylthio group, arylthio group and heteroarylthio group. The chromene compound having specific substituents introduced into the specific positions has been unknown. A description is subsequently given of these substituents.

<$R^3$>

$R^3$ is a second sulfur-containing substituent bonded to the 11-position of the indeno(2,1-f)naphtho(1,2-b)pyran structure and selected from the group consisting of thiol group, alkylthio group, alkoxyalkylthio group, haloalkylthio group, cycloalkylthio group, arylthio group, heteroarylthio group, alkylsulfonyl group, alkoxyalkylsulfonyl group, haloalkylsulfonyl group, cycloalkylsulfonyl group, arylsulfonyl group, heteroarylsulfonyl group, hydroxysulfonyl group, alkylsulfinyl group, alkoxyalkylsulfinyl group, haloalkylsulfinyl group, cycloalkylsulfinyl group, arylsulfinyl group, heteroarylsulfinyl group and hydroxysulfinyl group. A detailed description is subsequently given of the second sulfur containing substituent.

The above alkylthio group is preferably an alkylthio group having 1 to 6 carbon atoms. Preferred examples of the alkylthio group include methylthio group, ethylthio group, n-propylthio group, isopropylthio group, n-butylthio group, sec-butylthio group and tert-butylthio group.

The above alkoxyalkylthio group is preferably an alkylthio group having 1 to 6 carbon atoms and substituted by an alkoxy group having 1 to 3 carbon atoms. Preferred examples of the alkoxyalkylthio group include methoxymethylthio group, methoxyethylthio group, methoxy-n-propylthio group, methoxy-n-butylthio group, ethoxyethylthio group and n-propoxypropylthio group.

The above haloalkylthio group is preferably an alkylthio group having 1 to 6 carbon atoms and substituted by a fluorine atom, chlorine atom or bromine atom. Preferred examples of the haloalkylthio group include trifluoromethylthio group, tetrafluoroethylthio group, chloromethylthio group, 2-chloroethylthio group and bromomethylthio group.

The above cycloalkylthio group is preferably a cycloalkylthio group having 3 to 8 carbon atoms. Preferred examples of the cycloalkylthio group include cyclopropylthio group, cyclobutylthio group, cyclopentylthio group and cyclohexylthio group.

The above arylthio group is preferably an arylthio group having 6 to 10 carbon atoms. Preferred examples of the arylthio group include phenylthio group, 1-naphthylthio group and 2-naphthylthio group.

The above heteroarylthio group is preferably a heteroarylthio group having 4 to 12 carbon atoms. Preferred examples of the heteroarylthio group include thienylthio group, furylthio group, pyrrolylthio group, pyridylthio group, benzothienylthio group, benzofurylthio group and benzopyrrolylthio group.

One to nine hydrogen atoms, particularly preferably one to four hydrogen atoms of each of the above arylthio group and the above heteroarylthio group may be substituted by an alkyl group having 1 to 6 carbon atoms, alkoxy group having 1 to 6 carbon atoms, cycloalkyl group having 3 to 8 carbon atoms, or halogen atom.

The above alkylsulfonyl group is preferably an alkylsulfonyl group having 1 to 6 carbon atoms. Preferred examples of the alkylsulfonyl group include methylsulfonyl group, ethylsulfonyl group, n-propylsulfonyl group and n-butylsulfonyl group.

The above alkoxyalkylsulfonyl group is preferably an alkylsulfonyl group having 1 to 6 carbon atoms and substituted by an alkoxy group having 1 to 3 carbon atoms. Preferred examples of the alkoxyalkylsulfonyl group include methoxymethylsulfonyl group, methoxyethylsulfonyl group, methoxy-n-propylsulfonyl group, methoxy-n-butylsulfonyl group, ethoxyethylsulfonyl group and n-propoxypropylsulfonyl group.

The above haloalkylsulfonyl group is preferably an alkylsulfonyl group having 1 to 6 carbon atoms and substituted by a fluorine atom, chlorine atom or bromine atom. Preferred examples of the haloalkylsulfonyl group include trifluoromethylsulfonyl group, tetrafluoroethylsulfonyl group, chloromethylsulfonyl group, 2-chloroethylsulfonyl group and bromomethylsulfonyl group.

The above cycloalkylsulfonyl group is preferably a cycloalkylsulfonyl group having 3 to 8 carbon atoms. Preferred examples of the cycloalkylsulfonyl group include cyclopropylsulfonyl group, cyclobutylsulfonyl group, cyclopentylsulfonyl group and cyclohexylsulfonyl group.

The above arylsulfonyl group is preferably an arylsulfonyl group having 6 to 10 carbon atoms. Preferred examples of the arylsulfonyl group include phenylsulfonyl group, 1-napthylsulfonyl group, 2-naphthylsulfonyl group and p-toluenesulfonyl group.

The above heteroarylsulfonyl group is preferably a heteroarylsulfonyl group having 4 to 12 carbon atoms. Preferred examples of the heteroarylsulfonyl group include thienylsulfonyl group, furylsulfonyl group, pyrrolylsulfonyl group, pyridylsulfonyl group, benzothienylsulfonyl group, benzofurylsulfonyl group and benzopyrrolylsulfonyl group.

The above alkylsulfinyl group is preferably an alkylsulfinyl group having 1 to 6 carbon atoms. Preferred examples of the alkylsulfinyl group include methylsulfinyl group, ethylsulfinyl group, n-propylsulfinyl group and n-butylsulfinyl croup.

The above alkoxyalkylsulfinyl group is preferably an alkylsulfinyl group having 1 to 6 carbon atoms and substituted by an alkoxy group having 1 to 3 carbon atoms. Preferred examples of the alkoxyalkylsulfinyl group include methoxymethylsulfinyl group, methoxyethylsulfinyl group, methoxy-n-propylsulfinyl group, methoxy-n-butylsulfinyl group, ethoxyethylsulfinyl group and n-propoxypropylsulfinyl group.

The above haloalkylsulfinyl group is preferably an alkylsulfinyl group having 1 to 6 carbon atoms and substituted by a fluorine atom, chlorine atom or bromine atom. Preferred examples of the haloalkylsulfinyl group include trifluoromethylsulfinyl group, tetrafluoroethylsulfinyl group, chloromethylsulfinyl group, 2-chloroethylsulfinyl group and bromomethylsulfinyl group.

The above cycloalkylsulfinyl group is preferably a cycloalkylsulfinyl group having 3 to 8 carbon atoms. Preferred examples of the cycloalkylsulfinyl group include cyclopropylsulfinyl group, cyclobutylsulfinyl group, cyclopentylsulfinyl group and cyclohexylsulfinyl group.

The above arylsulfinyl group is preferably an arylsulfinyl group having 6 to 10 carbon atoms. Preferred examples of the arylsulfinyl group include phenylsulfinyl group, 1-naphthylsulfinyl group, 2-naphthylsulfinyl group and p-toluenesulfinyl group.

The above heteroarylsulfinyl group is preferably a heteroarylsulfinyl group having 4 to 12 carbon atoms. Preferred examples of the heteroarylsulfinyl group include thienylsulfinyl group, furylsulfinyl group, pyrrolylsulfinyl group, pyridylsulfinyl group, benzothienylsulfinyl group, benzofurylsulfinyl group and benzopyrrolylsulfinyl group.

<Preferred $R^3$>

Out of the groups represented by $R^3$, alkylthio groups, haloalkylthio groups, cycloalkylthio groups, alkylsulfonyl groups, cycloalkylsulfonyl groups, alkylsulfinyl groups and cycloalkylsulfinyl groups are preferred because excellent double peak characteristic and high fading speed are obtained and a compound which rarely experiences the reduction of color optical density is provided in the case of a combination of $R^1$ and $R^2$ which will be described hereinafter. More preferably, $R^3$ is a methylthio group, trifluoromethylthio group, cyclopropylthio group, methylsulfonyl group, cyclopropylsulfonyl group, methylsulfinyl group or cyclopropylsulfinyl group. Particularly preferably, $R^3$ is an alkylthio group or haloalkylthio group because excellent double peak characteristic and excellent color optical density are obtained. Most preferably, $R^3$ is a methylthio group or a trifluoromethylthio group.

<$R^1$ and $R^2$>

A combination of $R^1$ and $R^2$ is any one of (i) to (v).

Explanation of Combination (i)

The combination (i) is a combination of an aryl group or a heteroaryl group as $R^1$ and an electron donating group having a Hammett constant $\sigma_p$ of $-0.1$ or less as $R^2$. In the present invention, a chromene compound comprising the combination (i) has high color optical density and excellent durability.

(Explanation of $R^1$ in Combination (i): Group $R^1$)

The above aryl group is preferably an aryl group having 6 to 14 carbon atoms. Preferred examples of the aryl group include phenyl group, 1-naphthyl group, 2-naphthyl group, 1-phenanthryl group, 2-phenanthryl group, 1-anthryl group and 9-anthryl group.

The above heteroaryl group is preferably a heteroaryl group having 4 to 12 carbon atoms. The heteroaryl group is bonded to the carbon atom at the 6-position to form a carbon-carbon bond. Preferred examples of the heteroaryl group include thienyl group, furyl group, pyrrolinyl group, pyridyl group, benzothienyl group, benzofuryl group and benzopyrrolinyl group.

The hydrogen atoms, preferably 1 to 4 hydrogen atoms of the above aryl group or the above heteroaryl group may be substituted by a hydroxyl group, alkyl group, haloalkyl group, cycloalkyl group, alkoxy group, amino group, heterocyclic group having a ring member nitrogen atom and bonded to an aryl group or a heteroaryl group bonded thereto via the nitrogen atom, cyano group, nitro group, formyl group, hydroxycarbonyl group, alkylcarbonyl group, alkoxycarbonyl group, halogen atom, aralkyl group, aralkoxy group, aryl group or aryloxy group. A description is subsequently given of these substituents.

The alkyl group is preferably an alkyl group having 1 to 6 carbon atoms. Preferred examples of the alkyl group include methyl group, ethyl group, n-propyl group, isopropyl group, n-butyl group, sec-butyl group, tert-butyl group, pentyl group and hexyl group.

The haloalkyl group is preferably an alkylthio group having 1 to 6 carbon atoms and substituted by a fluorine atom, chlorine atom or bromine atom. Preferred examples of the haloalkyl group include trifluoromethyl group, pentafluoroethyl group, chloromethyl group, 2-chloroethyl group and bromomethyl group.

The cycloalkyl group is preferably a cycloalkyl group having 3 to 8 carbon atoms. Preferred examples of the cycloalkyl group include cyclopropyl group, cyclobutyl group, cyclopentyl group and cyclohexyl group.

The alkoxy group is preferably an alkoxy group having 1 to 6 carbon atoms. Preferred examples of the alkoxy group include methoxy group, ethoxy group, n-propoxy group, isopropoxy group, n-butoxy group, sec-butoxy group and tert-butoxy group.

The amino group is not limited to a primary amino group (—$NH_2$), and one or two hydrogen atoms of the primary amino group may be substituted. Examples of the substituent of the amino group include alkyl groups having 1 to 6 carbon atoms, alkoxy groups having 1 to 6 carbon atoms, cycloalkyl groups having 3 to 8 carbon atoms, aryl groups having 6 to 10 carbon atoms and heteroaryl groups having 4 to 12 carbon atoms. Examples of these substituents are the same as those enumerated for $R^1$ and its substituents. Preferred examples of the amino group include amino group, methylamino group, dimethylamino group, ethylamino group, diethylamino group, phenylamino group and diphenylamino group.

Preferred examples of the heterocyclic group having a ring member nitrogen atom and bonded to an aryl group or a heteroaryl group bonded thereto via the nitrogen atom include morpholino group, piperidino group, pyrrolidinyl group, piperazino group, N-methylpiperazino group and indolinyl group. Further, the heterocyclic group may have a group having a Hammett constant $\sigma_p$ of less than 0 as a substituent. Examples of the substituent include alkyl groups such as methyl group. Preferred examples of the heterocyclic group having a substituent include 2,6-d-methylmorpholino group, 2,6-dimethylpiperidino group and 2,2,6,6-tetramethylpiperidino group.

The alkylcarbonyl group is preferably an alkylcarbonyl group having 2 to 7 carbon atoms. Preferred examples thereof include acetyl group and ethylcarbonyl group.

The alkoxycarbonyl group is preferably an alkoxycarbonyl group having 2 to 7 carbon atoms. Preferred examples thereof include methoxycarbonyl group and ethoxycarbonyl group.

Examples of the halogen atom are fluorine atom, chlorine atom, bromine atom and iodine atom.

The aralkyl group is preferably an aralkyl group having 7 to 11 carbon atoms. Preferred examples of the aralkyl group include benzyl group, phenylethyl group, phenylpropyl group, phenylbutyl group and naphthylmethyl group.

The aralkoxy group is preferably an aralkoxy group having 7 to 11 carbon atoms. Preferred examples of the aralkoxy group include benzyloxy group and naphthylmethoxy group.

The aryl group is preferably an aryl group having 6 to 14 carbon atoms. Preferred examples of the aryl group include phenyl group, 1-naphthyl group and 2-naphthyl group.

The aryloxy group is preferably an aryloxy group having 6 to 10 carbon atoms. Preferred examples of the aryloxy group include phenoxy group, 1-naphthoxy group and 2-naphthoxy group.

<Preferred $R^1$ in (i): Preferred Group $R^1$>

Out of the groups represented by $R^1$, an aryl group having 6 to 14 carbon atoms is preferred because a compound having excellent double peak characteristic is provided. To obtain especially excellent double peak characteristic and high color optical density, 1 to 4 hydrogen atoms of the aryl group are substituted preferably by a substituent having a Hammett constant $\sigma_p$ of $-1.00$ or more to less than 0, particularly preferably by a substituent having a Hammett constant $\sigma_p$ of $-1.00$ or more to less than $-0.2$. Specific examples of the aryl group include aryl groups substituted by at least one group selected from the group consisting of hydroxyl group, alkoxy group, amino group, heterocyclic group having a ring member nitrogen atom and bonded to the 6-position carbon atom via the nitrogen atom, aralkoxy group and aryloxy group. Out of these, an aryl group substituted by at least one group selected from the group consisting of hydroxyl group, alkoxy group, amino group, heterocyclic group having a ring member nitrogen atom and bonded to the 6-position carbon atom via the nitrogen atom and aryloxy group is preferred. An aryl group substituted by at least one group selected from the group consisting of alkoxy group, amino group and heterocyclic group having a ring member nitrogen atom and bonded to the 6-position carbon atom via the nitrogen atom is more preferred. Particularly preferred examples of the aryl group include 4-methoxyphenyl group, 2,4-dimethoxyphenyl group, 4-(N,N-dimethylamino)phenyl group and 4-morpholinophenyl group.

(Explanation of $R^2$ in Combination (i): Group $R^2$)

$R^2$ is an electron donating group having a Hammett constant $\sigma_p$ of $-0.1$ or less. $R^2$ which is an electron donating group having a Hammett constant $\sigma_p$ of $-0.1$ or less is a hydroxyl group ($\sigma_p=-0.37$), alkyl group, cycloalkyl group, alkoxy group, aryloxy group, aralkyl group, aralkoxy group, amino group or heterocyclic group having a ring member nitrogen atom and bonded to the 7-position carbon atom via the nitrogen atom.

A detailed description is subsequently given of the above electron donating group having a Hammett constant $\sigma_p$ of $-0.1$ or less.

The alkyl group is generally a group having a $\sigma_p$ of $-0.2$ to $-0.1$. It is particularly preferably an alkyl group having 1 to 6 carbon atoms. Further, 1 to 13, particularly preferably 1 to 4 hydrogen atoms of the alkyl group may be substituted by the above hydroxyl group, alkoxy group, amino group or heterocyclic group having a ring member nitrogen atom and bonded to an alkyl group substituted thereby via the nitrogen atom all of which have been explained for the substituent of $R^1$. The above heterocyclic group substituting an alkyl group is the same as the heterocyclic group substituting an aryl group or a heteroaryl group which has been explained in <substituent of $R^1$>. The substituent having a ring member nitrogen atom and bonded via the nitrogen atom is defined the same. Preferred examples of the alkyl group include methyl group ($\sigma_p=-0.10$), ethyl group ($\sigma_p=-0.20$), n-propyl group ($\sigma_p=-0.12$), isopropyl group, n-butyl group, sec-butyl group, tert-butyl group ($\sigma_p=-0.15$), pentyl group and hexyl group. Preferred examples of the substituted alkyl group include hydroxymethyl group, methoxymethyl group, N,N-dimethylaminomethyl group and morpholinomethyl group.

The cycloalkyl group is generally a group having a $\sigma_p$ of $-0.2$ to $-0.1$. It is particularly preferably a cycloalkyl group having 3 to 20 carbon atoms in the present invention. Further, 1 to 39, particularly preferably 1 to 20 hydrogen atoms of the cycloalkyl group may be substituted by the above hydroxyl group, alkoxy group, amino group, heterocyclic group having a ring member nitrogen atom and bonded to a cycloalkyl group substituted thereby via the nitrogen atom or halogen atom all of which have been explained for the substituent of $R^1$. Preferred examples of the cycloalkyl group include cyclopropyl group, cyclobutyl group, cyclopentyl group and cyclohexyl group ($\sigma_p=-0.16$). Preferred examples of the substituted cycloalkyl group include 4-hydroxycyclohexyl group, 4-methoxycyclohexyl group and 4-morpholinocyclohexyl group.

The alkoxy group is generally a group having a $\sigma_p$ of $-0.3$ to $-0.2$. It is particularly an alkoxy group having 1 to 15 carbon atoms. Further, 1 to 31, particularly preferably 1 to 10 hydrogen atoms of the alkoxy group may be substituted by the above hydroxyl group, alkoxy group, amino group, heterocyclic group having a ring member nitrogen atom and bonded to an alkoxy group substituted thereby via the nitrogen atom or halogen atom all of which have been explained for the substituent of $R^1$. Preferred examples of the alkoxy group include methoxy group ($\sigma_p=-0.28$), ethoxy group ($\sigma_p=-0.21$), n-propoxy group ($\sigma_p=-0.26$), isopropoxy group, n-butoxy group, sec-butoxy group, tert-butoxy group, cyclopropyloxy group, cyclobutyloxy group, cyclopentyloxy group, cyclohexyloxy group, norbornyloxy group, 1-adamantyloxy group and 2-adamantyloxy group. Examples of the substituted alkoxy group include methoxymethoxy group, N,N-dimethylaminomethoxy group and morpholinomethoxy group.

The amino group is generally a group having a $\sigma_p$ of $-1.0$ to $-0.5$. The preferred amino group may be either a primary amino group (—$NH_2$) ($\sigma_p=-0.66$) or a substituted secondary or tertiary amino group. Examples of the substituent of the amino group include alkyl groups having 1 to 6 carbon atoms, haloalkyl groups having 1 to 6 carbon atoms, alkoxy groups having 1 to 15 carbon atoms, cycloalkyl groups having 3 to 15 carbon atoms, halogen atoms, aryl groups having 6 to 10 carbon atoms and heteroaryl groups having 4 to 12 carbon atoms. The haloalkyl groups, the aryl groups and the heteroaryl groups are the same as those enumerated for the substituent of $R^1$. Other examples are the same as those enumerated for the substituent of $R^2$. Preferred examples of the secondary or tertiary amino group having one or two substituents include monoalkylamino groups such as methylamino group ($\sigma_p=-0.77$) and ethylamino group; dialkylamino groups such as dimethylamino group ($\sigma_p=-0.8$) and diethylamino group; monoarylamino groups such as phenylamino group ($\sigma_p=-0.11$); diarylamino groups such as diphenylamino group; halogenoamino groups such as difluoroamino group; and haloalkylamino groups such as bis(trifluoromethyl)amino group.

The heterocyclic group having a ring member nitrogen atom and bonded to the 7-position carbon atom via the nitrogen atom is generally a group having a $\sigma_p$ of $-1.0$ to $-0.4$. Preferred examples of the heterocyclic group include morpholino group ($\sigma_p=-0.50$), piperidino group ($\sigma_p=-0.83$), pyrrolidinyl group, piperazino group, N-methylpiperazino group and indolinyl group. The heterocyclic group may have an alkyl group having 1 to 6 carbon atoms, haloalkyl group having 1 to 6 carbon atoms, alkoxy group having 1 to 15 carbon atoms, cycloalkyl group having 3 to 15 carbon atoms, halogen atom, aryl group having 6 to 10 carbon atoms or heteroaryl group having 4 to 12 carbon atoms as a substituent. Examples of the haloalkyl group, the aryl group and the heteroaryl group are the same as those enumerated for the substituent of $R^1$. Other examples are the same as those enumerated for the substituent of $R^2$. Specific examples of the substituent include alkyl groups such as methyl group. Examples of the heterocyclic group having a substituent include 2,6-dimethylmorpholino group, 2,6-dimethylpiperidino group, 2,2,6,6-tetramethylpiperidino group, 2-fluoromorpholino group and 2,6-difluoromorpholino group.

The aryloxy group is generally a group having a $\sigma_p$ of $-0.5$ to $-0.2$. It is particularly preferably an aryloxy group having 6 to 10 carbon atoms. Preferred examples of the aryloxy group include phenoxy group ($\sigma_p=-0.32$) and 1-naphthoxy group.

The aralkyl group is generally a group having a $\sigma_p$ of $-0.1$ or less. It is particularly preferably an aralkyl group having 7 to 11 carbon atoms. Preferred examples of the aralkyl group include benzyl group, phenylethyl group, phenylpropyl group, phenylbutyl group and naphthylmethyl group.

The aralkoxy group is generally a group having a $\sigma_p$ of $-0.1$ or less. It is particularly preferably an aralkoxy group having 7 to 11 carbon atoms. Preferred examples of the aralkoxy group include benzyloxy group and naphthylmethoxy group.

One or more hydrogen atoms on the benzene ring of each of the above aryloxy group, the aralkyl group and the aralkoxy group may be substituted by an alkyl group having 1 to 6 carbon atoms, cycloalkyl group having 3 to 15 carbon atoms, alkoxy group having 1 to 15 carbon atoms, amine group or heterocyclic group having a ring member nitrogen atom and bonded to a carbon atom substituted thereby via the nitrogen atom. Examples of these substituents are the same as those enumerated for $R^2$. The aryloxy group, aralkyl group and aralkoxy group substituted by any one of these substituents have a $\sigma_p$ of $-0.1$ or less.

<Preferred $R^2$ in (i): Preferred Group $R^2$>

Out of the groups represented by $R^2$, preferred $R^2$ is a substituent having a $\sigma_p$ of $-0.2$ or less in combination with $R^1$ because a compound having excellent double peak characteristic and high color optical density is provided. Preferred examples of the group include hydroxyl group, alkoxy group, aryloxy group, amino group and heterocyclic group having a ring member nitrogen atom and bonded to the 7-position carbon atom via the nitrogen atom. More preferred examples of $R^2$ include hydroxyl group, methoxy group, phenoxy group, morpholino group, piperidino group and dimethylamino group. Further, a substituent having a $\sigma_p$ of $-0.6$ to $-0.2$ is preferred because it reduces initial coloration by thermochromism and accelerates the fading speed. The substituent is particularly preferably an alkoxy group, aryloxy group, amino group or heterocyclic group having a ring member nitrogen atom and bonded to the 7-position carbon atoms via the nitrogen atom all of which have a $\sigma_p$ of $-0.6$ to $-0.2$. Most preferred examples of the substituent include methoxy group, phenoxy group, difluoroamino group and morpholino group.

(Preferred Combination (i) of $R^1$ and $R^2$)

As a preferred combination (i), $R^1$ is the above preferred group $R^1$ and $R^2$ is an electron donating group having a Hammett constant $\sigma_p$ of $-0.1$ or less, $R^1$ is an aryl group or a heteroaryl group and $R^2$ is the above preferred group $R^2$, or $R^1$ is the above preferred group $R^1$ and $R^2$ is the above preferred group $R^2$.

(Explanation of Combination (ii))

As the combination (ii), $R^1$ is an electron donating group having a Hammett constant $\sigma_p$ of $-0.1$ or less, and $R^2$ is an aryl group or a heteroaryl group.

Examples of the electron donating group having a Hammett constant $\sigma_p$ of $-0.1$ or less as $R^1$ are the same as those enumerated in (explanation of $R^2$ in combination (i): group $R^2$).

Examples of the aryl group or heteroaryl group as $R^2$ are the same as those enumerated in (explanation of $R^1$ in combination (i): group $R^1$).

<Preferred Combination (ii) of $R^1$ and $R^2$>

As a preferred combination, $R^1$ is an electron donating group having a Hammett constant $\sigma_p$ of $-0.1$ or less (explanation of $R^2$ in combination (i): group $R^2$) and $R^2$ is the same as the group explained in the above preferred group $R^1$, $R^1$ is the same as the group explained in the above preferred group $R^2$ and $R^2$ is the same as the group explained in (explanation of $R^1$ in combination (i): group $R^1$), or $R^1$ is the same as the group explained in the above preferred group $R^2$ and $R^2$ is the same as the group explained in the above preferred group $R^1$.

The reasons that the above groups are preferred are the same as in (i).

In the present invention, this combination (ii) provides a compound which can have highest color development sensitivity.

Explanation of Combination (iii)

As the combination (iii), both of $R^1$ and $R^2$ are each a first sulfur-containing substituent selected from the group consisting of thiol group, alkylthio group, alkoxyalkylthio group, haloalkylthio group, cycloalkylthio group, arylthio group and heteroarylthio group.

The above alkylthio group, alkoxyalkylthio group, haloalkylthio group, cycloalkylthio group, arylthio group and heteroarylthio group are the same as those explained as the second sulfur-containing substituent.

Out of the above first sulfur-containing substituents, an alkylthio group having 1 to 6 carbon atoms, an alkylthio group having 1 to 6 carbon atoms and substituted by an alkoxy group having 1 to 3 carbon atoms or a cycloalkylthio group having 3 to 8 carbon atoms is preferred because color optical density becomes high, double peak characteristic becomes high and initial coloration is reduced by positioning the absorption end at a short wavelength range and suppressing thermochromism. Further, an alkylthio group having 1 to 6 carbon atoms or a cycloalkylthio group having 3 to 8 carbon atoms is particularly preferred as color optical density and double peak characteristic in particular are enhanced. Particularly preferred examples of these groups include methylthio group, ethylthio group and cyclohexylthio group.

A thiol group or a haloalkylthio group having 1 to 6 carbon atoms is preferred so as to increase the fading speed and reduce initial coloration by thermochromism. A haloalkylthio group having 1 to 6 carbon atoms is more preferred. More specifically, a trifluoromethylthio group is particularly preferred.

When a combination of $R^1$ and $R^2$ is (iii), the chromene compound of the present invention which is particularly notable in that it is excellent in double peak characteristic and durability and has little initial coloration by the positioning of the absorption end at a short wavelength range and the reduction of thermochromism and high fading speed is obtained.

Explanation of Combination (iv)

As the combination (iv), $R^1$ is the above first sulfur-containing substituent. This preferred first sulfur-containing substituent is the same as the group explained in (iii).

In the above combination (iv), $R^2$ is a hydrogen atom, hydroxyl group, alkyl group, haloalkyl group, cycloalkyl group, alkoxy group, amino group, heterocyclic group having a ring member nitrogen atom and bonded to a carbon atom bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group. Specific examples of these groups are the same as those enumerated for $R^1$ in the combination (i).

When $R^2$ is a hydroxyl group, alkyl group, cycloalkyl group, alkoxy group, amino group, heterocyclic group having a ring member nitrogen atom and bonded to the 7-position carbon atom via the nitrogen atom, aralkyl group, aralkoxy group, aryloxy group or aryl group out of the groups represented by $R^2$, the double peak characteristic becomes higher than that when $R^2$ is a group other than these groups. $R^2$ is preferably a hydroxyl group, alkoxy group, amino group, heterocyclic group having a ring member nitrogen atom and bonded to the 7-position carbon atom via the nitrogen atom or aryloxy group so as to enhance double peak characteristic and color optical density in particular and reduce initial coloration by positioning the absorption end at a short wavelength range. Further, $R^2$ is more preferably an alkoxy group or heterocyclic group having a ring member nitrogen atom and bonded to the 7-position carbon atom via the nitrogen atom. It is particularly preferably a methoxy group or morpholino group.

When a combination of $R^1$ and $R^2$ is (iv), the chromene compound of the present invention which is particularly notable in that it is excellent in double peak characteristic and durability and has little initial coloration by positioning the absorption end at a short wavelength range and high fading speed is obtained.

Explanation of Combination (v)

As the combination (v), $R^2$ is the above first-sulfur containing substituent. This preferred first sulfur-containing substituent is the same as the group explained in (iii).

Further, in the above combination (v), $R^1$ is a hydrogen atom, hydroxyl group, alkyl group, haloalkyl group, cycloalkyl group, alkoxy group, amino group, aliphatic heterocyclic group having a ring member nitrogen atom and bonded to the 6-position carbon atom via the nitrogen atom, cyano group, nitro group, formyl group, hydroxycarbonyl group, alkylcarbonyl group, alkoxycarbonyl group, halogen atom, aralkyl group, aralkoxy group or aryloxy group. Specific examples of these groups are the same as those explained for $R^1$ in the combination (i).

When $R^1$ is a hydroxyl group, alkyl group, cycloalkyl group, alkoxy group, amino group, aliphatic heterocyclic group having a ring member nitrogen atom and bonded to the 6-position carbon atom via the nitrogen atom, aralkyl group, aralkoxy group or aryloxy group out of the above groups represented by $R^1$, double peak characteristic becomes higher than that when $R^1$ is a group other than these groups. $R^1$ is preferably a hydroxyl group, alkoxy group, amino group, heterocyclic group having a ring member nitrogen atom and bonded to the 6-position carbon atom via the nitrogen atom or aryloxy group so as to enhance double peak characteristic and color optical density. $R^1$ is more preferably an alkoxy group or heterocyclic group having a ring member nitrogen atom and bonded to the 6-position carbon atom via the nitrogen atom. It is particularly preferably a methoxy group or morpholino group.

When a combination of $R^1$ and $R^2$ is (v), the chromene compound of the present invention which is particularly notable in that it is excellent in double peak characteristic and durability and has little initial coloration by the reduction of thermochromism and high fading speed is obtained.

<Preferred Chromene Compound>

Out of the chromene compounds of the present invention, a chromene compound represented by the following formula (2) is preferred as it develops a color of a neutral tint and has little initial coloration, high double peak characteristic and a small reduction in color optical density though it has high fading speed, and high durability.

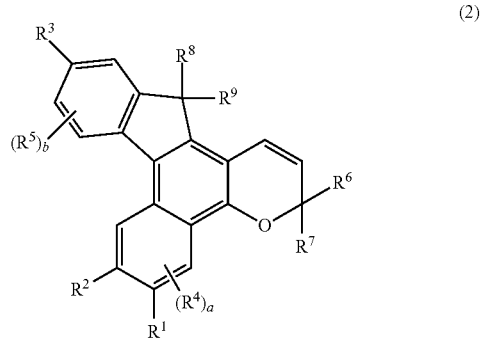

(2)

The substituents $R^1$ to $R^9$ of the chromene compound represented by the above formula (2) will be described hereinbelow.

<$R^1$ and $R^2$>

$R^1$ and $R^2$ are as defined in the above formula (1).

When a combination of $R^1$ and $R^2$ is (iii), $R^1$ and $R^2$ may be the same or different and preferred examples of the groups are the same as those explained for the above combination (iii).

When a combination of $R^1$ and $R^2$ is any one of (i) and (ii), a preferred combination of $R^1$ and $R^2$ is the same as the preferred combination given above.

(Compound Represented by the Above Formula (2) when a Combination of $R^1$ and $R^2$ is (iv))

When a combination of $R^1$ and $R^2$ is (iv) in the above formula (2), a chromene compound represented by the following formula (2iv) is preferred so as to exhibit an excellent effect.

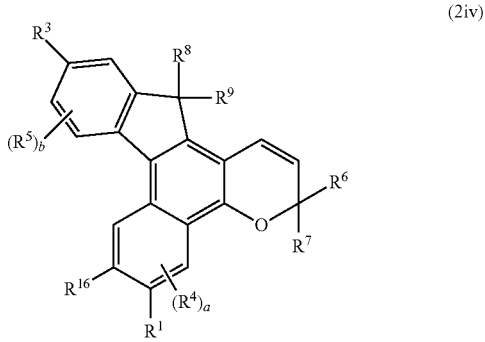

(2iv)

$R^1$ is defined the same as $R^1$ of the combination (iv) in the above formula (1), and $R^{16}$ is an electron donating group having a Hammett constant $\sigma_p$ of −0.50 to −0.01 out of the groups defined as $R^2$ of the combination (iv) in the above formula (1).

$R^1$ in the above formula (2iv) is defined the same as $R^1$ of (iv) in the above formula (1), that is, the above first sulfur-containing substituent. As a matter of course, preferred $R^1$ is the same as the group explained for the above first sulfur-containing substituent.

$R^{16}$ in the above formula (2iv) is an electron donating group having a Hammett constant $\sigma_p$ of −0.50 to −0.01 selected from hydrogen atom, hydroxyl group, alkyl group, haloalkyl group, cycloalkyl group, alkoxy group, amino group, heterocyclic group having a ring member nitrogen atom and bonded to the 7-position carbon atom bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group. When the chromene compound has the electron donating group which satisfies this requirement, double peak characteristic can be enhanced while initial coloration is suppressed.

Examples of $R^{16}$ include heterocyclic groups having a ring member nitrogen atom and bonded to the 7-position carbon atom via the nitrogen atom such as morpholino group ($\sigma_p=-0.50$), alkoxy groups such as methoxy group ($\sigma_p=-0.28$), ethoxy group ($\sigma_p=-0.21$) and propoxy group ($\sigma_p=-0.26$), p-alkylaminophenyl groups such as p-dimethylaminophenyl group ($\sigma_p=-0.22$) and p-diethylaminophenyl group ($\sigma_p=-0.22$), alkoxyphenyl groups such as p-methoxyphenyl group ($\sigma_p=-0.04$) and o,p-dimethoxyphenyl group ($\sigma_p=-0.08$), aryl groups such as phenyl group ($\sigma_p=-0.51$), 1-naphthyl group ($\sigma_p=-0.08$) and 2-naphthyl group ($\sigma_p=-0.02$), p-nitrogen atom-containing heterocyclic aryl groups such as p-morpholinophenyl group ($\sigma_p=-0.16$), heteroaryl groups such as thienyl group ($\sigma_p=1$), alkyl groups such as methyl group ($\sigma_p=-0.14$), ethyl group ($\sigma_p=-0.13$) and propyl group ($\sigma_p=-0.12$), and cycloalkyl groups such as cyclohexyl group ($\sigma_p=-0.16$).

Out of these, groups having a $\sigma_p$ of −0.50 to −0.02 are preferred, groups having a $\sigma_p$ of −0.50 to −0.10 are more preferred, and groups having a $\sigma_p$ of −0.50 to −0.20 are particularly preferred because initial coloration and double peak characteristic are well balanced. Particularly preferred examples of these groups include alkoxy groups such as methoxy group and ethoxy group, and aliphatic heterocyclic groups having a ring member nitrogen atom and bonded to the 7-position carbon atom via the nitrogen atom such as morpholino group in consideration of the above point.

In the present invention, the above $R^{16}$ is preferred in order to obtain an optical article having little initial coloration and high transparency. Separately from this, to obtain a compound having high color development sensitivity, groups having a $\sigma_p$ of −0.40 to −0.01 are more preferred, groups having a $\sigma_p$ of −0.30 to −0.01 are much more preferred, and groups having a $\sigma_p$ of −0.20 to −0.01 are particularly preferred. Particularly preferred examples of these groups include aryl groups such as phenyl group and naphthyl group, alkoxyphenyl groups such as p-methoxyphenyl group and o,p-dimethoxyphenyl group, p-nitrogen atom-containing heterocyclic aryl groups such as p-morpholinophenyl group, heteroaryl groups such as thienyl group, alkyl groups such as methyl group, ethyl group and propyl group, and cycloalkyl groups such as cyclohexyl group:

(Compound Represented by the Above Formula (2) when a Combination of $R^1$ and $R^2$ is (v))

In the above formula (2), when a combination of $R^1$ and $R^2$ is (v), a chromene compound represented by the following formula (2v) is preferred so as to exhibit an excellent effect.

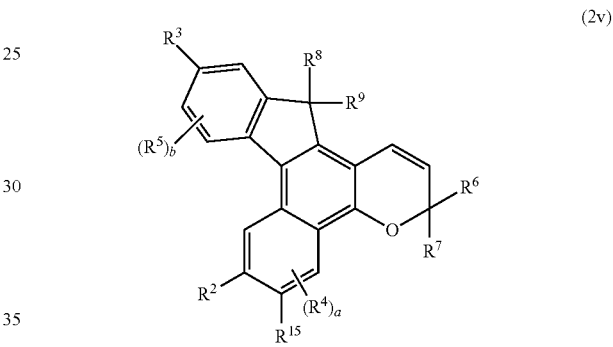

(2v)

$R^2$ is defined the same as $R^2$ of (v) in the above formula (1).

$R^{15}$ is an electron donating group having a Hammett constant $\sigma_p$ of −0.50 to −0.01 out of the groups defined as $R^1$ of (v) in the above formula (1).

$R^2$ in the above formula (2v) is defined the same as $R^2$ of (v) in the above formula (1), that is, the above first sulfur-containing substituent. As a matter of course, the preferred croup is the same as the group explained for the above first sulfur-containing substituent.

$R^{15}$ in the above formula (2v) is an electron donating group having a Hammett constant $\sigma_p$ of −0.50 to −0.01 selected from hydrogen atom, hydroxyl group, alkyl group, haloalkyl group, cycloalkyl group, alkoxy group, amino group, aliphatic heterocyclic group having a ring member nitrogen atom and bonded to the 6-position carbon atom bonded thereto via the nitrogen atom, cyano group, nitro group, formyl group, hydroxycarbonyl group, alkylcarbonyl group, alkoxycarbonyl group, halogen atom, aralkyl group, aralkoxy group or aryloxy group. When the chromene compound has an electron donating group which satisfies this requirement, double peak characteristic can be enhanced while initial coloration is suppressed.

Examples of $R^{15}$ include aliphatic heterocyclic groups having a ring member nitrogen atom and bonded to the 6-position carbon atom via the nitrogen atom such as morpholino group ($\sigma_p=-0.50$), alkoxy groups such as methoxy group ($\sigma_p=-0.28$), ethoxy group ($\sigma_p=-0.21$) and propoxy group ($\sigma_p=-0.26$), alkyl groups such as methyl group ($\sigma_p=-0.14$), ethyl group ($\sigma_p=-0.13$) and propyl group ($\sigma_p=-0.12$), and cycloalkyl groups such as cyclohexyl group ($\sigma_p=-0.16$).

Out of these, groups having a $\sigma_p$ of −0.50 to −0.02 are preferred, groups having a $\sigma_p$ of −0.50 to −0.10 are more preferred, and groups having a $\sigma_p$ of −0.50 to −0.20 are particularly preferred because initial coloration and double peak characteristic are well balanced. Particularly preferred examples of these groups include alkoxy groups such as methoxy group and ethoxy group, and aliphatic heterocyclic groups having a ring member nitrogen atom and bonded to the 6-position carbon atom via the nitrogen atom such as morpholino group in consideration of the above point.

In the formulas (2iv) and 2 (v), $R^3$, $R^4$, $R^5$, $R^6$, $R^7$, $R^6$, $R^9$, "a" and "b" are as defined in the above formula (2). These groups will be described in derail hereinunder.

<$R^3$>

In the above formula (2), $R^3$ is a second sulfur-containing substituent. Examples of the group are the same as those enumerated above. Also, preferred examples are the same as above.

<$R^4$ and $R^5$>

$R^4$ and $R^5$ are each independently a hydroxyl group, alkyl group, haloalkyl group, cycloalkyl group, alkoxy group, amino group, heterocyclic group having a ring member nitrogen atom and bonded to a carbon atom bonded thereto via the nitrogen atom, cyano group, nitro group, formyl group, hydroxycarbonyl group, alkylcarbonyl group, alkoxycarbonyl group, halogen atom, aralkyl group, aralkoxy group, aryl group or aryloxy group.

Out of these, $R^4$ and $R^5$ are each preferably an alkyl group having 1 to 6 carbon atoms, haloalkyl group having 1 to 6 carbon atoms, cycloalkyl group having 3 to 15 carbon atoms, alkoxy group having 1 to 15 carbon atoms, amino group, heterocyclic group having a ring member nitrogen atom and bonded to a carbon atom bonded thereto via the nitrogen atom, alkylcarbonyl group having 2 to 7 carbon atoms, alkoxycarbonyl group having 2 to 7 carbon atoms, halogen atom, aralkyl group having 7 to 11 carbon atoms, aralkoxy group having 7 to 11 carbon atoms, aryl group having 6 to 10 carbon atoms or aryloxy group having 6 to 10 carbon atoms. Specific examples of these groups are the same as those enumerated above.

Particularly preferably, $R^4$ has a stereoscopically small substituent as high fading speed is provided. Therefore, particularly preferred $R^4$ is a hydrogen atom ("a" is 0).

Meanwhile, $R^5$ is preferably a hydrogen atom ("b" is 0) as high fading speed is obtained.

"a" is an integer of 0 to 2 indicative of the number of the group $R^4$'s. When "a" is 2, two $R^4$'s may be the same or different. "b" is an integer of 0 to 3 indicative of the number of the group $R^5$'s. When "b" is an integer of 2 or 3, a plurality of $R^5$'s may be the same or different. When there are a plurality of $R^4$'s or a plurality of $R^5$'s, preferred $R^4$'s and $R^5$'s are the same as those enumerated above.

<$R^6$ and $R^7$>

$R^6$ and $R^7$ are each independently a group represented by the following formula (3), group represented by the following formula (4), aryl group, heteroaryl group or alkyl group.

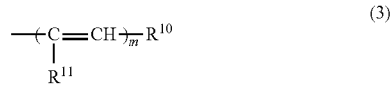

(3)

(4)

In the above formula (3), $R^{10}$ is an aryl group or a heteroaryl group. The aryl group and the heteroaryl group are the same as those enumerated above. Also, preferred examples of the groups are the same as those enumerated above.

$R^{11}$ is a hydrogen atom, alkyl group or halogen atom. Examples of the alkyl group include methyl group, ethyl group and propyl group. Examples of the halogen atom are fluorine atom, chlorine atom, bromine atom and iodine atom.

"m" is an integer of 1 to 3. From the viewpoint of the acquisition of the raw material, "m" is preferably 1.

Preferred examples of the group represented by the above formula (3) include phenyl-ethenyl group, (4-(N,N-dimethylamino)phenyl)-ethenyl group, (4-morpholinophenyl)-ethenyl group, (4-piperidinophenyl)-ethenyl group, (4-methoxyphenyl)-ethenyl group, (2-methoxyphenyl)-ethenyl group, phenyl-1-methylethenyl group, (4-methoxyphenyl)-1-methylethenyl group, phenyl-1-fluoroethenyl group, (4-(N,N,-dimethylamino)phenyl)-1-fluoroethenyl group, 2-thienyl-ethenyl group, 2-furyl-ethenyl group, 2-(N-methyl)pyrrolinyl-ethenyl group, 2-benzothienyl-ethenyl group, 2-benzofuranyl-ethenyl group and 2-(N-methyl)indolyl-ethenyl group.

In the above formula (4), $R^{12}$ is an aryl group or a heteroaryl group. Examples of these groups are the same as those enumerated above. Preferred examples thereof are the same as those enumerated above. "n" is an integer of 1 to 3. From the viewpoint of the easy acquisition of the raw material, "n" is preferably 1.

Preferred examples of the group represented by the above formula (4) include phenyl-ethynyl group, (4-(N,N-dimethylamino)phenyl)-ethynyl group, (4-morpholinophenyl)-ethynyl group, (4-piperidinophenyl)-ethynyl group, (4-methoxyphenyl)-ethynyl group, (4-methylphenyl)-ethynyl group, (2-methoxyphenyl)-ethynyl group, 2-thienyl-ethynyl group, 2-furyl-ethynyl group, 2-(N-methyl)pyrrolinyl-ethynyl group, 2-benzothienyl-ethyl group, 2-benzofuranyl-ethynyl group and 2-(N-methyl)indolyl-ethynyl group.

Examples of the aryl group, the heteroaryl group and the alkyl group represented by $R^6$ and $R^7$ are the same as those enumerated above. Also, preferred examples of these groups are the same as those enumerated above.

$R^6$ and $R^7$ may be bonded together to form an aliphatic hydrocarbon ring together with the carbon atom bonded thereto.

Preferred examples of the aliphatic hydrocarbon ring include adamantane ring, bicyclononane ring, norbornane ring and fluorene ring.

In order to obtain excellent photochromic properties (double peak characteristic and fading speed), desirably, at least one, preferably both of $R^6$ and $R^7$ are aryl groups or heteroaryl groups. Particularly preferably, at least one, preferably both of $R^6$ and $R^7$ are each anyone of the following groups (p1) to (p3):

(p1) an aryl group or heteroaryl group having an alkyl group or alkoxy group as a substituent;

(p2) an aryl group or heteroaryl group having an amino group as a substituent;

(p3) an aryl group or heteroaryl group having a heterocyclic group which has a ring member nitrogen atom and is bonded to an aryl group or a heteroaryl group via the nitrogen atom as a substituent.

The substitution positions and the total number of substituents in the aryl groups (p1) to (p3) are not particularly limited. In order to obtain excellent photochromic properties, when the aryl group is a phenyl group, the substitution position is preferably the 3-position or 4-position of the phenyl group, and the number of substituents is preferably 1 or 2. Examples of this aryl group include 4-methylphenyl group, 4-methoxyphenyl group, 3,4-dimethoxyphenyl group, 4-n-propoxyphenyl group, 4-(N,N-dimethylamino)phenyl group, 4-(N,N-diethylamino)phenyl group, 4-(N,N-diphenylamino) phenyl group, 4-morpholinophenyl group, 4-piperidinophenyl group, 3-(N,N-dimethylamino)phenyl group and 4-(2,6-dimethylpiperidino)phenyl group.

The substitution positions and the total number of substituents in the heteroaryl groups (p1) to (p3) are not particularly limited. The number of the substituents is preferably 1. Preferred examples of the heteroaryl group include 4-methoxythienyl group, 4-(N,N-dimethylamino)thienyl group, 4-methylfuryl group, 4-(N,N-diethylamino)furyl group, 4-(N,N-diphenylamino)thienyl group, 4-morpholinopyrrolinyl group, 6-piperidinobenzothienyl group and 6-(N,N-dimethylamino)benzofuryl group.

<$R^8$ and $R^9$>

$R^8$ and $R^9$ are each independently a hydrogen atom, hydroxyl group, alkyl group, haloalkyl group, cycloalkyl group, alkoxy group, amino group, heterocyclic group having a ring member nitrogen atom and bonded to the 13-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryl group or aryloxy group.

Out of the above groups, $R^8$ and $R^9$ are each preferably an alkyl group having 1 to 6 carbon atoms, haloalkyl group having 1 to 6 carbon atoms, cycloalkyl group having 3 to 15 carbon atoms, alkoxy group having 1 to 15 carbon atoms, amino group, heterocyclic group having a ring member nitrogen atom and bonded to the 13-position carbon atom via the nitrogen atom, alkylcarbony group having 2 to 7 carbon atoms, alkoxycarbonyl group having 2 to 7 carbon atoms, halogen atom, aralkyl group having 7 to 11 carbon atoms, aralkoxy group having 7 to 11 carbon atoms, aryl group having 6 to 10 carbon atoms or aryloxy group having 6 to 10 carbon atoms.

Examples thereof are the same as those enumerated above. Also, preferred examples thereof are the same as those enumerated above.

$R^8$ and $R^9$ may be bonded together to form an aliphatic ring having 3 to 20 ring member carbon atoms, condensed polycyclic ring having an aromatic ring or aromatic hetero ring condensed to the aliphatic ring, hetero ring having 3 to 20 ring member atoms, or condensed polycyclic ring having an aromatic ring or aromatic hetero ring condensed to the hetero ring, together with the 13-position carbon atom bonded thereto.

Examples of the above aliphatic ring having 3 to 20 ring member carbon atoms include cyclopentane ring, cyclohexane ring, cyclooctane ring, cycloheptane ring, norbornane ring, bicyclononane ring and adamantane ring.

Examples of the above condensed polycyclic ring having an aromatic ring or aromatic hetero ring condensed to the above aliphatic ring include phenanthrene ring.

Examples of the above hetero ring having 3 to 20 ring member atoms include dihydrothiophene ring, dihydrofuran ring, tetrahydrofuran ring and dihydropyridine ring.

Examples of the above condensed polycyclic ring having an aromatic ring or aromatic hetero ring condensed to the above hetero ring include dihydrobenzofuran ring and dihydrobenzothiophene ring.

<Particularly Preferred $R^8$ and $R^9$>

In the present invention, preferred substituents $R^8$ and $R^9$ are each a hydroxyl group, alkyl group, alkoxy group or substituent which forms a ring together with the 13-position carbon atom bonded thereto. An example of the alkyl group is methyl group and an example of the alkoxy group is methoxy group. To increase the fading speed and reduce initial coloration by thermochromism while retaining high color optical density and high double peak characteristic, out of the above preferred substituents, $R^8$ and $R^9$ are preferably substituents which form a ring together with the 13-position carbon atom. They are particularly preferably substituents which form the above aliphatic ring or the condensed polycyclic ring having an aromatic ring or aromatic hetero ring condensed to the above aliphatic ring as the fading speed in particular becomes high. They are most preferably substituents which form the above aliphatic ring as the fading speed becomes highest and initial coloration by thermochromism is reduced.

The aliphatic ring formed by $R^8$ and $R^9$ together with the 13-position carbon atom is particularly preferably an aliphatic hydrocarbon ring having 3 to 20 ring member carbon atoms. This aliphatic hydrocarbon ring may have at least one substituent selected from the group consisting of alkyl group having 1 to 6 carbon atoms, haloalkyl group having 1 to 6 carbon atoms, cycloalkyl group having 3 to 15 carbon atoms, alkoxy group having 1 to 15 carbon atoms, amino group, aralkyl group having 7 to 11 carbon atoms, aryl group having 6 to 10 carbon atoms and halogen atom. Such a substituted aliphatic hydrocarbon ring is also preferred. Examples of the alkyl group, haloalkyl group, cycloalkyl group, alkoxy group, amino group, aralkyl group, aryl group and halogen atom are the same as those enumerated above. Also preferred groups are the same as those enumerated above.

More preferred examples of the aliphatic hydrocarbon ring include monocyclic rings such as cyclopentane ring, cyclohexane ring, cycloheptane ring, cyclooctane ring and cyclononane ring, bicycle rings such as norbornane ring and bicyclononane ring, and tricyclo rings such as adamantane ring. These rings having at least one lower alkyl group having 4 or less carbon atoms such as methyl group are also preferred. Out of these, monocyclic rings exhibit a particularly excellent effect as initial coloration by thermochromism is reduced while high color optical density, high double peak characteristic and high fading speed are retained.

In the present invention, most preferred typical examples of the ring formed by bonding $R^8$ and $R^9$ together with the 13-position carbon atom bonded thereto include rings represented by the following formulas. In the following formulas, the carbon atom at a position denoted by 13 is the 13-position carbon atom of the above pyran structure.

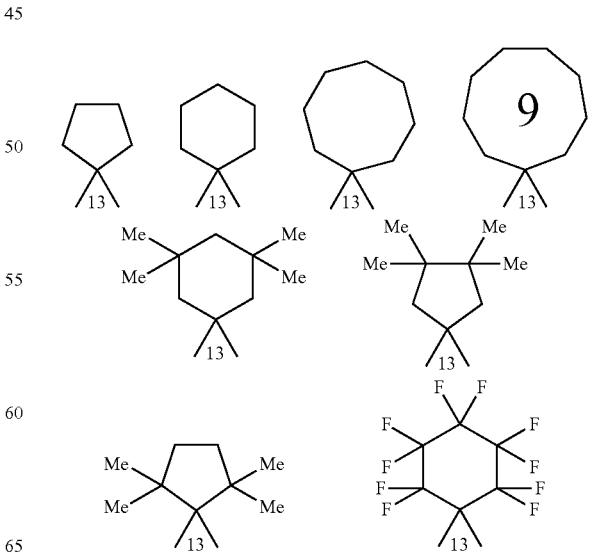

Out of the above monocyclic rings, a cyclooctane ring, cyclononane ring and 3,3,5,5-tetramethylcyclohexane ring are most preferred.

<Particularly Preferred Examples of Chromene Compound>

Particularly preferred examples of the chromene compound in the present invention include the following compounds.

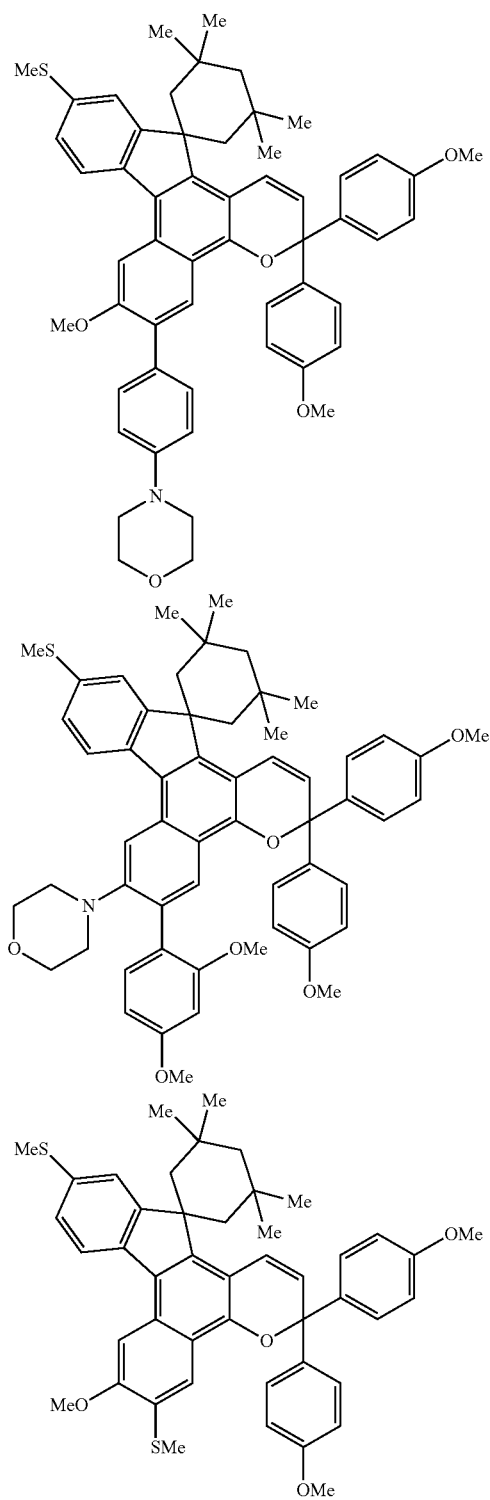

(Identification of Chromene Compound)

The chromene compound of the present invention is generally existent as an achromatic, light yellow or light green solid or viscous liquid at normal temperature and normal pressure and can be confirmed by the following means (1) to (3).

(1) When the proton nuclear magnetic resonance spectrum ($^1$H-NMR) of the chromene compound is measured, peaks based on an aromatic proton and an alkene proton appear at δ of around 5.0 to 9.0 ppm and peaks based on the protons of an alkyl group and an alkylene group appear at δ of around 1.0 to 4.0 ppm. By comparing these spectral intensities relatively, the number of the protons of bonds can be known.

(2) The composition of a corresponding product can be determined by elemental analysis.

(3) When the $^{13}$C-nuclear magnetic resonance spectrum ($^{13}$C-NMR) of the chromene compound is measured, a peak based on the carbon of an aromatic hydrocarbon group appears at δ of around 110 to 160 ppm, peaks based on the carbons of an alkene and an alkyne appear at δ of around 80 to 140 ppm, and peaks based on the carbons of an alkyl group and an alkylene group appear at δ of around 20 to 80 ppm.

<Production of Chromene Compound>

The chromene compound of the present invention may be produced by any synthesis process. For example, the chromene compound represented by the above formula (2) can be advantageously produced by the following process. In the following description, the symbols in the following formulas are as defined in the above formulas unless otherwise noted.

The chromene compound can be advantageously produced by reacting a naphthol compound represented by the following formula (5) with a propargyl alcohol compound represented by the following formula (6) in the presence of an acid catalyst.

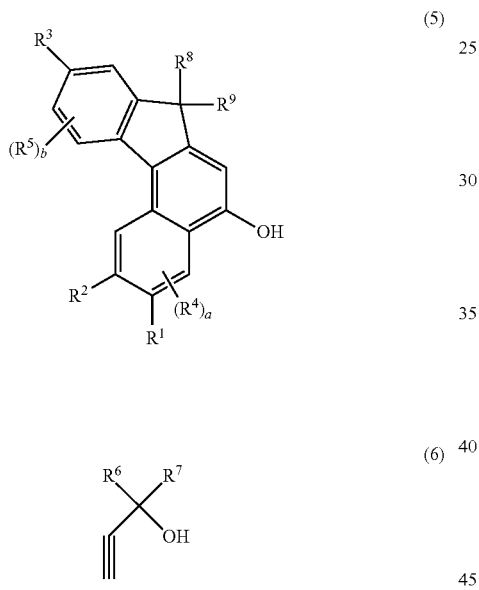

The reaction ratio of the naphthol compound to the propargyl alcohol compound is preferably selected from a range of 1:10 to 10:1 (molar ratio). As the acid catalyst is used sulfuric acid, benzenesulfonic acid, p-toluenesulfonic acid or acid alumina. The acid catalyst is preferably used in an amount of 0.1 to 10 parts by weight based on 100 parts by weight of the total of the naphthol compound and the propargyl alcohol compound. The reaction temperature is preferably 0 to 200° C. An aprotic organic solvent such as N-methylpyrrolidone, dimethyl formamide, tetrahydrofuran, benzene or toluene is preferably used as the solvent. The method of purifying the product obtained through the above reaction is not particularly limited. For example, the obtained product may be purified by carrying out silica gel column purification and further recrystallization.

The naphthol compound represented by the above formula (5) is provided as a novel compound by the present invention.

Preferred examples of the naphthol compound represented by the formula (5) include the following compounds.

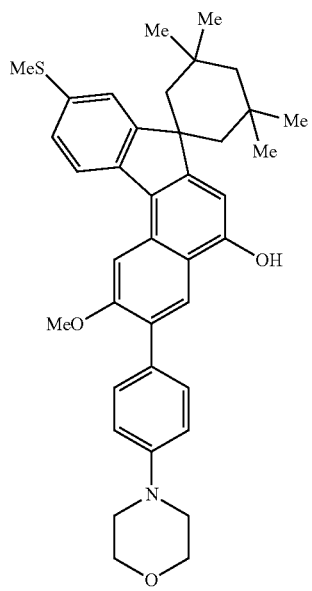

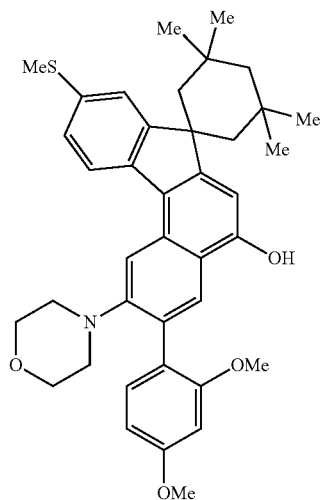 [SMILES: COc1ccc(-c2cc3c(O)cc4c(c3cc2N2CCOCC2)-c2ccc(SC)cc2C42CC(C)(C)CC(C)(C)C2)c(OC)c1]

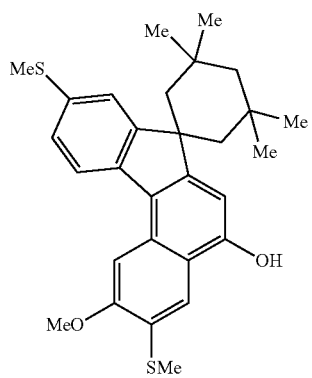

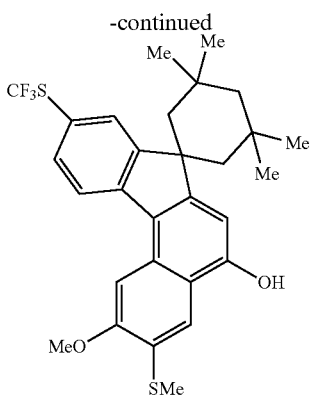

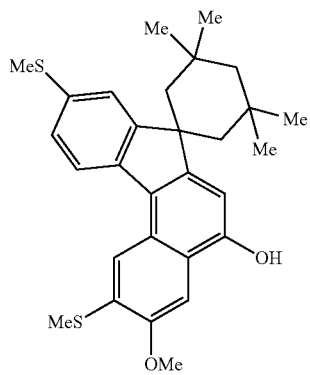

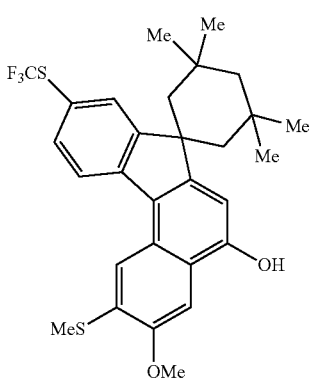

<Synthesis Method of Naphthol Compound>

Ordinary naphthol compounds can be synthesized in accordance with reaction methods described in, for example, research papers such as a pamphlet of International Laid-Open WO01/60881 and a pamphlet of International Laid-Open WO05/028465.

The naphthol compound represented by the above formula (5) in which a combination of $R^1$ and $R^2$ is (i) or (ii) can be synthesized as follows, for example.

To begin with, a carboxylic acid represented by the following formula (7) may be purchased as a commercial product or may be synthesized based on the following documents ($R^4$ and "a" are as defined in the above formula (2)). $X^1$ is a halogen atom or the same as $R^1$ in the formula (2). $X^2$ is a halogen atom or the same as $R^2$ in the formula (2)).

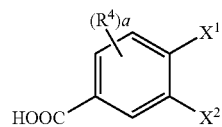

For example, a carboxylic acid represented by the following formula (8) can be purchased as a commercial product.

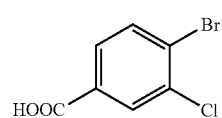

For example, a carboxylic acid represented by the following formula (9) can be synthesized in accordance with a reaction method described in research papers such as Journal of the Chemical Society. 20-27; 1927.

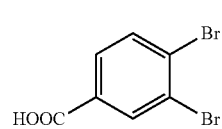

A compound represented by the following formula (10) ($R^5$ and "b" are as defined in the above formula (2)) is produced by reacting the compound (7) with thionyl chloride or oxalyl chloride to obtain acid chloride and reacting the acid chloride with a Grignard reagent, and then when $X^1$ and $X^2$ are each a chlorine atom, bromine atom or iodine atom, they are converted into desired $R^1$ and $R^2$ by using a Suzuki-Miura reaction or Buchwald-Hartwig cross-coupling reaction to obtain a compound represented by the following formula (11).

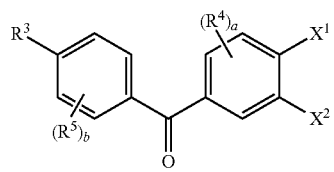

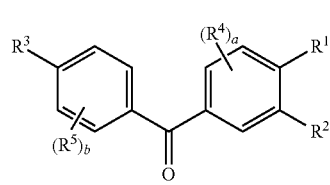

A compound represented by the following formula (12) is obtained by subjecting the above compound (II) to a Stobbe reaction and a cyclization reaction.

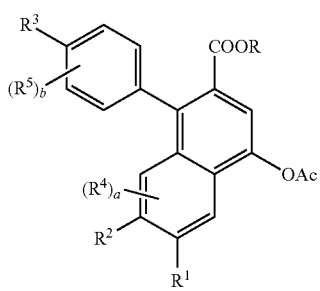
(12)

In the compound of the formula (12), R is a group derived from a diester compound used in the Stobbe reaction. Then, the compound (12) is hydrolyzed by using an alkali or acid to obtain a carboxylic acid represented by the following formula (13).

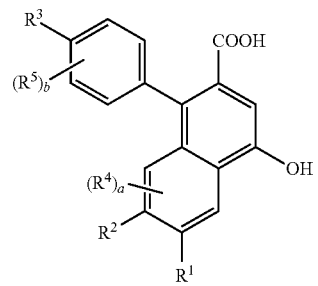
(13)

This carboxylic acid is benzylated by using a base such as potassium carbonate and benzyl chloride and then hydrolyzed by using an alkali or acid to obtain a benzyl-protected carboxylic acid represented by the following formula (14). Bn in the formula (14) is a benzyl group.

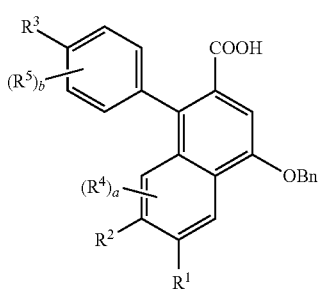
(14)

This benzyl-protected carboxylic acid is converted into an amine by a method such as Curtius rearrangement, Hofmann rearrangement or Lossen rearrangement, and a diazonium salt is prepared from the amine by a method known per se. This diazonium salt is converted into a bromide through a Sandmeyer reaction or the like, and the obtained bromide is reacted with magnesium or lithium to prepare an organic metal compound. This organic metal compound is reacted with a ketone represented by the following formula (15) at −80 to 70° C. in an organic solvent for 10 minutes to 4 hours and then a debenzylation reaction is carried out by using hydrogen and palladium carbon to obtain an alcohol represented by the following formula (16).

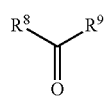
(15)

($R^8$ and $R^9$ are as defined in the above formula (2).)

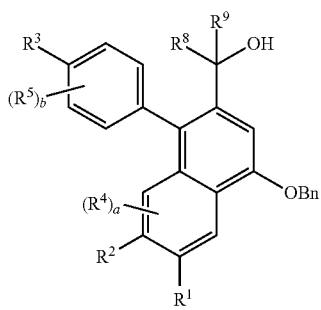
(16)

This alcohol is subjected to a Friedel-Crafts reaction at 10 to 120° C. for 10 minutes to 2 hours under a neutral to acid condition so as to synthesize the naphthol compound of the above formula (5) of interest. In the above reaction, the reaction ratio of the above organic metal compound to the ketone represented by the above formula (15) is preferably selected from a range of 1:10 to 10:1 (molar ratio). The reaction temperature is preferably −80 to 70° C. An aprotic organic solvent such as diethyl ether, tetrahydrofuran, benzene or toluene is preferably used as the solvent. The Friedel-Crafts reaction of the alcohol of the above formula (16) under a neutral to acid condition is preferably carried out by using an acid catalyst such as acetic acid, hydrochloric acid, sulfuric acid, benzenesulfonic acid, p-toluenesulfonic acid or acid alumina. The acid catalyst is preferably used in an amount of 0.1 to 10 parts by weight based on 100 parts by weight of the alcohol of the above formula (16). For this reaction, an aprotic organic solvent such as tetrahydrofuran, benzene or toluene is used. A naphthol compound represented by the above formula (5) is synthesized through this reaction.

When a combination of $R^1$ and $R^2$ is any one of (iii) to (v), for example, a benzophenone compound represented by the above formula (11) can be synthesized as follows.

To begin with, a benzene compound represented by the following formula (17) may be purchased as a commercial product or may be synthesized based on the following documents ($R^1$, $R^2$, $R^4$ and "a" are as defined in the above formula (2)).

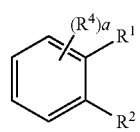
(17)

For example, benzene compounds represented by the following formulas (18a) and (18b) can be purchased as commercial products.

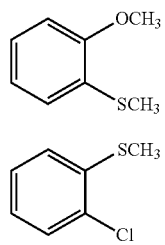

(18a)

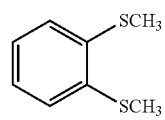

(18b)

For example, a benzene compound represented by the following formula (19) can be synthesized in accordance with a reaction method described in research papers such as Organometallics. 8.(5). 1303-1308; 1989.

(19)

The benzophenone compound represented by the above formula (11) ($R^3$, $R^5$ and "b" are as defined in the above formula (2)) is obtained by reacting the compound (17) with acid chloride.

To determine the positions of $R^1$ and $R^2$ in the obtained naphthol compound of the formula (5), the types of the substituents in the formula (17) and the degree of electron donating ability of each substituent are preferably adjusted. For example, when the same sulfur-containing substituent is used as $R^1$ and $R^2$, the benzene compound represented by the formula (19) should be used, when the electron donating ability of $R^1$ is made higher than the electron donating ability of $R^2$, the benzene compound represented by the formula (18a) should be used, and when the electron donating ability of $R^1$ is made lower than the electron donating ability of $R^2$, the benzene compound represented by the formula (18b) should be first used to produce the compound represented by the formula (11) and then the chlorine atom should be converted into desired $R^2$ by using a Buchwald-Hartwig cross-coupling reaction after the step of producing the compound of the formula (11).

The naphthol compound represented by the above formula (5) can be synthesized by applying the steps after the above Stobbe reaction using the benzophenone compound obtained as described above.

The propargyl alcohol compound represented by the above formula (6) can be easily synthesized by reacting a ketone compound corresponding to the above formula (6) with a metal acetylene compound such as lithium acetylide.

The chromene compound of the present invention which is synthesized as described above dissolves well in a general organic solvent such as toluene, chloroform or tetrahydrofuran. When the chromene compound represented by the above formula (1) is dissolved in such a solvent, the obtained solution is generally almost achromatic and transparent and has an excellent photochromic function that it develops a color swiftly upon exposure to sunlight or ultraviolet radiation and reversibly returns to its original achromatic state swiftly by blocking the light.

(Combination with Another Photochromic Compound>

Although the chromene compound of the present invention develops a color of a neutral tint by itself, it may be used in combination with another photochromic compound to obtain various colors required as a photochromic lens. Any known compound may be used as the photochromic compound to be combined with. Examples of the photochromic compound include fulgide, fulgimide, spirooxazine and chromene. Out of these, a chromene compound is particularly preferred because it can keep a color uniformly at the time of color development and fading, can suppress a color drift at the time of color development due to the deterioration of photochromic properties and further can reduce initial coloration.

That is, by combining the chromene compound of the present invention with another chromene compound which has high color optical density, high fading speed and little initial coloration like the above chromene compound, a photochromic composition which keeps a color uniformly at the time of color development and fading and provides high transparency can be obtained.

To provide high transparency, the chromene compound to be combined with preferably has a transmittance by thermochromism of 75% or more and an absorption end of an ultraviolet absorption curve at 380 to 430 nm. Further, a chromene compound having a transmittance by thermochromism of 85% or more and an absorption end of an ultraviolet absorption curve at 380 to 420 nm is particularly preferred, and a chromene compound having a transmittance by thermochromism of 88% or more and an absorption end of an ultraviolet absorption curve at 380 to 410 nm is most preferred. The transmittance by thermochromism and the absorption end of the ultraviolet absorption curve are values measured by methods described in the following examples.

Examples of the preferred chromene compound to be combined with include chromene compounds represented by the following formulas (20) and (21).

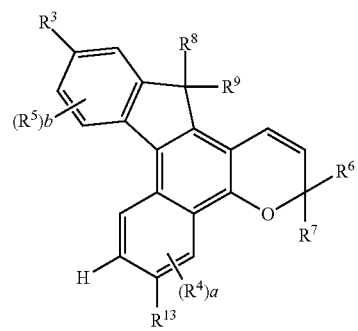

(20)

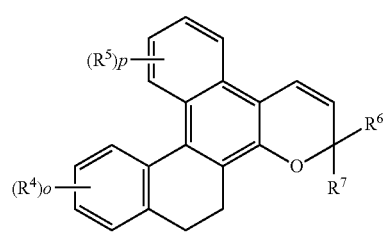

(21)

In the above formula (20), $R^3$, $R^4$, $R^5$, $R^6$, $R^7$, $R^8$, $R^9$, "a" and "b" are as defined in the above formula (2), and $R^{13}$ is a hydrogen atom, hydroxyl group, alkyl group, haloalkyl group, cycloalkyl group, alkoxy group, amino group, heterocyclic group having a ring member nitrogen atom and bonded to a carbon atom bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group. Specific examples of the chromene compound of the above formula (20) include compounds described in a pamphlet of International Laid-Open WO2001/60811.

In the above formula (21), $R^4$, $R^5$, $R^6$ and $R^7$ are as defined in the above formula (2), and "o" and "p" are each independently an integer of 0 to 4. Specific examples of the chromene compound of the above formula (21) include compounds described in a pamphlet of International Laid-Open WO2009/136668.

To obtain a photochromic composition comprising the chromene compound of the present invention and another chromene compound, the ratio of these chromene compounds may be suitably determined according to a desired color. In this case, the amount of the chromene compound of the present invention or another chromene compound is preferably 0.001 to 10 parts by mass based on 100 parts by mass of the total of all the polymerizable monomers. Stated more specifically, in the case of a thin film such as a coating film, for example, a thin film having a thickness of about 100 μm, color control should be carried out by using 0.001 to 5.0 parts by mass of the chromene compound of the present invention and 0.001 to 5.0 parts by mass of another chromene compound based on 100 parts by mass of the coating film or the total of all the polymerizable monomers which provide the coating film. In the case of a thick cured material, for example, a cured material having a thickness of 1 mm or more, color control should be carried out by using 0.001 to 0.5 part by mass of the chromene compound of the present invention and 0.001 to 0.5 part by mass of another chromene compound based on 100 parts by mass of the thick cured material or the total of all the polymerizable monomers which provide the thick cured material.

(Stabilizer to be Combined with)

Although the chromene compound of the present invention has high durability as it is, its durability can be further enhanced by using the following ultraviolet absorbent, optical stabilizer or antioxidant. As the ultraviolet absorbent may be used known ultraviolet absorbents such as benzophenone compounds, benzotriazole compounds, cyanoacrylate compounds, triazine compounds and benzoate compounds. Cyanoacrylate compounds and benzophenone compounds are particularly preferred. When the above ultraviolet absorbent is used in an amount of 0.001 to 5 parts by mass based on 100 parts by mass of the total of all the polymerizable monomers including the chromene compound of the present invention, it exhibits an effect. Known hindered amines may be used as the optical stabilizer, and known hindered phenols may be used as the antioxidant. When the above optical stabilizer and antioxidant are each used in an amount of 0.01 to 10 parts by mass based on 100 parts by mass of the total of all the polymerizable monomers including the chromene compound of the present invention, they exhibit an effect.

(Use of Chromene Compound>

A photochromic composition comprising the chromene compound of the present invention and the chromene compound represented by the above formula (1), (20) or (21) exhibits the same photochromic properties even in a polymer solid matrix. The polymer solid matrix is not particularly limited if the chromene compound of the present invention can be uniformly dispersed therein. Examples of the optically preferred polymer compound for the polymer solid matrix include thermoplastic resins such as methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethylmethacrylate), polydimethylsiloxane and polycarbonate.

The photochromic composition comprising the chromene compound of the present invention and the chromene compound represented by the above formula (1), (20) or (21) may be mixed with polymerizable monomers before polymerization to obtain a photochromic curable composition which is then polymerized and cured to obtain a photochromic composition. That is, a photochromic curable composition comprising the photochromic composition of the present invention and polymerizable monomers may be polymerized and cured to obtain a cured material containing the photochromic composition uniformly dispersed therein.

A photochromic curable composition which is prepared by mixing a photochromic composition comprising the chromene compound represented by the above formula (1), (20) or (21) with the following polymerizable monomers (A1), (A2) and (A3) and provides a cured material having an L scale Rockwell hardness of 60 or more is preferred because it exhibits excellent photochromic properties such as high color optical density and high fading speed and obtains excellent substrate properties such as high hardness and high heat resistance:

(A1) a polymerizable monomer which has an L scale Rockwell hardness of a polymer obtained by homopolymerizing it of 40 or less,
(A2) a trifunctional or higher functional radically polymerizable monomer which has an L scale Rockwell hardness of a polymer obtained by homopolymerizing it of 60 or more, and
(A3) a bifunctional radically polymerizable monomer having an L scale Rockwell hardness of a polymer obtained by homopolymerizing it of 60 or more.

Examples of the component (A1) include acrylate compounds and methacrylate compounds such as glycidyl acrylate, glycidyl methacrylate, β-methylglycidyl methacrylate, bisphenol A-monoglycidyl ether-methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate and 3-glycidyloxy-2-hydroxypropyloxy)-2-hydroxypropyl acrylate, and polyalkylene glycol compounds such as polyethylene glycol diacrylate. Examples of the component (A2) include polyacrylate and polymethacrylate compounds such as trimethylolpropane trimethacrylate, urethane acrylates such as urethane oligomer tetramethacrylate, and polyester acrylates such as polyester oligomer hexaacrylate. Examples of the component (A3) include polyacrylate and polymethacrylate compounds such as ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl)propane and 2,2-bis(3,5-dibromo-4-methacryloyloxyethoxyphenyl) propane, all of which are polymerizable monomers described in a pamphlet of International Laid-Open WO2001/05854. The term "L scale Rockwell hardness" means hardness measured in accordance with JIS-B7726, and it can be easily judged whether the above hardness condition is satisfied or not by measuring the homopolymer of each monomer.

Copolymers obtained by copolymerizing the above polymerizable monomers with polymerizable monofunctional monomers may also be used as the above polymer matrix. The polymerizable monofunctional monomers include unsaturated carboxylic acids such as acrylic acid, methacrylic acid and maleic anhydride; polyallyl compounds such as diallyl phthalate, diallyl terephthalate, diallyl isophthalate, diallyltartarate, diallyl epoxysuccinate, diallyl fumarate, diallyl chlorendate, diallyl hexaphthalate, diallyl carbonate, allyl diglycol carbonate and trimethylolpropane triallyl carbonate; polythioacrylate and polythiomethacrylate compounds such as 1,2-bis(methacryloylthio)ethane, bis(2-acryloylthioethyl) ether and 1,4-bis(methacryloylthiomethyl)benzene; acrylate and methacrylate compounds such as methyl acrylate, methyl methacrylate, benzyl methacrylate, phenyl methacrylate and 2-hydroxyethyl methacrylate; fumarate compounds such as diethyl fumarate and diphenyl fumarate; thioacrylate and thiomethacrylate compounds such as methyl thioacrylate, benzyl thioacrylate and benzyl thiomethacrylate; and vinyl compounds such as styrene, chlorostyrene, methyl styrene, vinyl naphthalene, α-methylstyrene dimer and bromostyrene. They may be used alone or in combination of two or more, and the amount of each of the monomers may be suitably determined according to use purpose.

The method of dispersing the chromene compound of the present invention into the above polymer solid matrix is not particularly limited, and commonly used methods may be employed. The methods include one in which the above thermoplastic resin and the chromene compound are kneaded together while they are molten to disperse the chromene compound into the resin, one in which the chromene compound is dissolved in the above polymerizable monomers and a polymerization catalyst is added to polymerize the polymerizable monomers by heat or light so as to disperse the chromene compound into the resin, and one in which the surfaces of the above thermoplastic resin and the above thermosetting resin are dyed with the chromene compound to disperse the chromene compound into the resins.

(Other Applications of the Chromene Compound of the Present Invention)

The chromene compound of the present invention can be widely used in photochromic materials such as recording materials as substitutes for silver halide photosensitive materials, copy materials, printing photosensitive materials, recording materials for cathode ray tubes, photosensitive materials for lasers and photosensitive materials for holography. A photochromic material comprising the chromene compound of the present invention may also be used as a photochromic lens material, optical filter material, display material or material for actinometers and ornaments.

For instance, when the chromene compound of the present invention is used in a photochromic lens, a method in which uniform light control performance is obtained, for example, a method in which a polymer film containing the photochromic material of the present invention uniformly dispersed therein is sandwiched between lenses, a method in which the chromene compound of the present invention is dispersed into the above polymerizable monomers and the polymerizable monomers are polymerized by a predetermined technique, or a method in which the chromene compound of the present invention is dissolved in, for example, silicone oil, the resulting solution is impregnated into the surface of a lens at 150 to 200° C. over 10 to 60 minutes, and the surface is further coated with a curable substance to obtain a photochromic lens may be employed. Further, a method in which the above polymer film is formed on the surface of a lens and the surface is coated with a curable substance to obtain a photochromic lens may also be employed.

Moreover, a coating agent composed of a polymerization curable composition comprising the chromene compound of the present invention may be applied to the surface of a lens substrate and cured. At this point, the lens substrate may be subjected to a surface treatment with an alkaline solution or a plasma treatment in advance, and a primer may be further applied so as to improve adhesion between the substrate and the coating film (by carrying out or not carrying out the above surface treatment).

EXAMPLES

The following examples are provided for the purpose of further illustrating the present invention but are in no way to be taken as limiting.

Synthesis of Chromene Compound

Example 1

1.20 g (2.0 mmol) of a naphthol compound represented by the following formula (22) and 0.80 g (3.0 mmol) of a propargyl alcohol compound represented by the following formula (23) were dissolved in 70 ml of toluene, 0.022 g of p-toluenesulfonic acid was further added to the resulting solution, and the obtained mixture was stirred under reflux by heating for 1 hour.

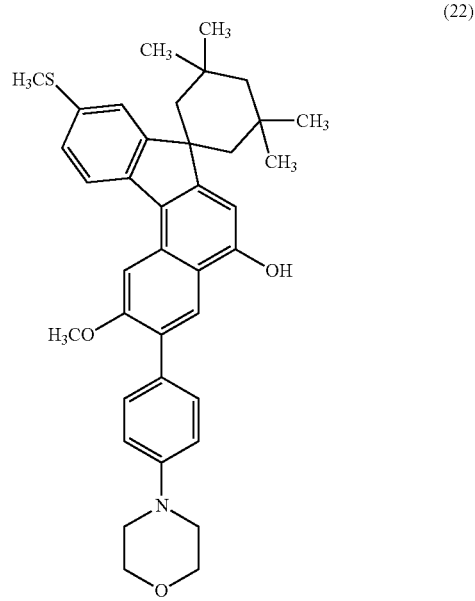

(22)

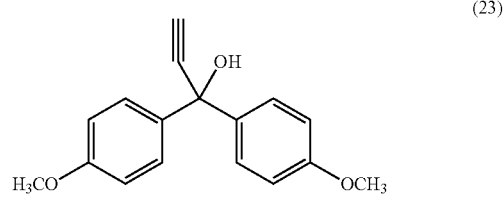

(23)

After a reaction, the solvent was removed, and the obtained product was purified on silica gel by chromatography to obtain 1.35 g of a white powder product. The yield was 80%.

The elemental analysis values of this product were 78.22%; of C, 6.72%; of H, 1.55%; of N and 3.75%; of S which were almost equal to the calculated values of $C_{52}H_{52}O_6$ (C, 78.26%; H, 6.81%; N, 1.66%; O, 9.48%; S, 3.80%).

When the proton nuclear magnetic resonance spectrum of the product was measured, it showed 18H peaks based on the methyl proton and methylene proton of a tetramethylcyclohexane ring at δ of around 1.0 to 3.0 ppm, 20H peaks based on the methyl proton of a methoxy group, the methyl proton of a methylthio group and the ethylene proton of a morpholino group at δ of around 2.3 to 5.0 ppm and 19H peaks based on an aromatic proton and an alkene proton at δ of around 5.6 to 9.0 ppm. Further, when the $^{13}C$-nuclear magnetic resonance spectrum was measured, it showed a peak based on the carbon of an aromatic ring at δ of around 110 to 160 ppm, a peak based on the carbon of an alkene at δ of around 80 to 140 ppm and a peak based on the carbon of an alkyl at δ of around 20 to 60 ppm.

It was confirmed from the above results that the isolated product was a compound represented by the following formula (24).

Synthesis of Chromene Compound (24)

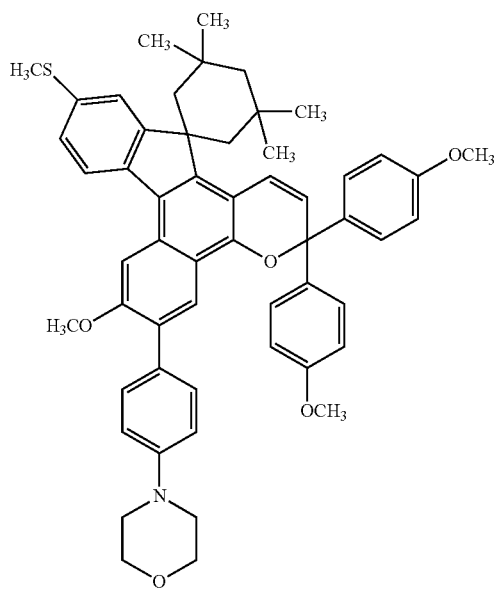

Examples 2 to 16

Chromene compounds shown in Tables 1 to 5 were synthesized in the same manner as in Example 1. When the structures of the obtained products were analyzed by using the same structure confirming means as in Example 1, it was confirmed that they were compounds represented by structural formulas shown in Tables 1 to 5. Table 6 shows the elemental analysis values, calculated values obtained from the structural formulas and characteristic $^1$H-NMR spectra of these compounds.

TABLE 1

| Example No. | Raw materials | | Product | Yield (%) |
|---|---|---|---|---|
| | Naphthol compound | Propargyl alcohol compound | | |
| 2 | 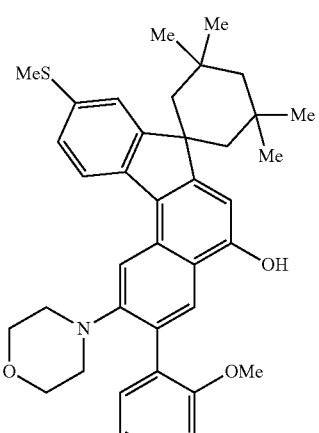 | 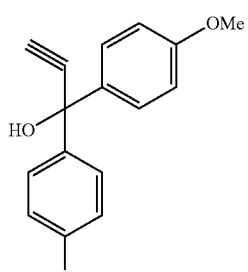 | 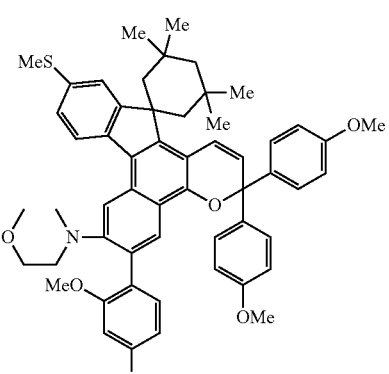 | 77 |

TABLE 1-continued
| Example No. | Raw materials | | Product | Yield (%) |
|---|---|---|---|---|
| | Naphthol compound | Propargyl alcohol compound | | |
| 3 | 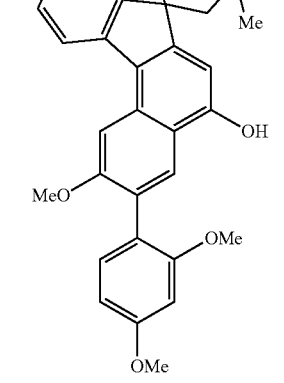 | 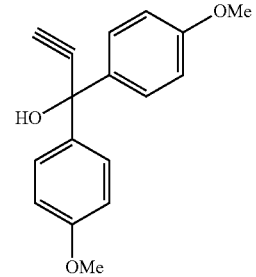 | 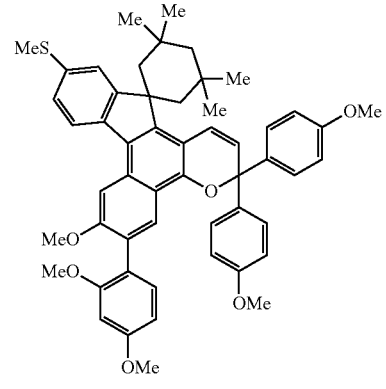 [SMILES: COc1ccc(C2(c3ccc(OC)cc3)C=Cc3c4c(c5cc(OC)c(-c6ccc(OC)cc6OC)cc5c3O2)-c2ccc(SC)cc2C42CC(C)(C)CC(C)(C)C2)cc1] | 75 |
| 4 | 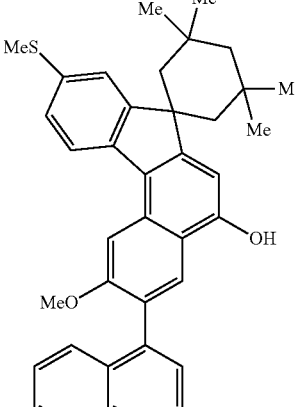 | 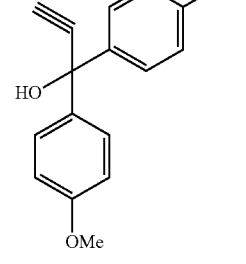 | 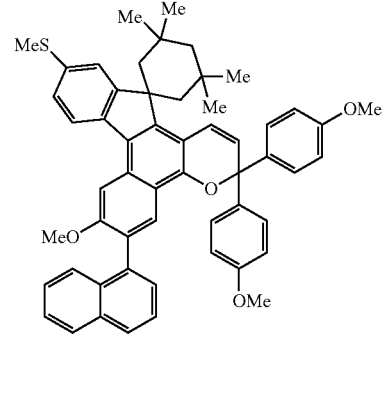 [SMILES: COc1ccc(C2(c3ccc(OC)cc3)C=Cc3c4c(c5cc(OC)c(-c6cccc7ccccc67)cc5c3O2)-c2ccc(SC)cc2C42CC(C)(C)CC(C)(C)C2)cc1] | 70 |

TABLE 2

| Example No. | Raw materials — Naphthol compound | Propargyl alcohol compound | Product | Yield (%) |
|---|---|---|---|---|
| 5 | (structure) | (structure) | (structure) | 73 |
| 6 | (structure) | (structure) | (structure) | 74 |
| 7 | (structure) | (structure) | (structure) | 68 |

TABLE 3

| Example No. | Raw materials | | Product | Yield (%) |
|---|---|---|---|---|
| | Naphthol compound | Propargyl alcohol compound | | |
| 8 | [structure] | [structure] | [structure] | 71 |
| 9 | [structure] | [structure] | [structure] | 68 |

TABLE 3-continued
| Example No. | Raw materials | | Product | Yield (%) |
|---|---|---|---|---|
| | Naphthol compound | Propargyl alcohol compound | | |
| 10 | 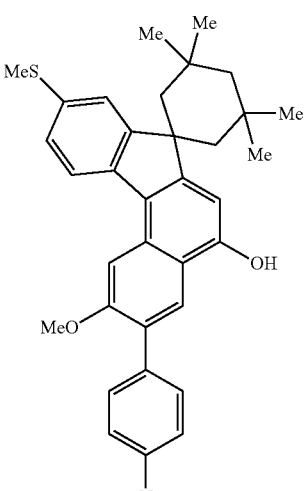 | 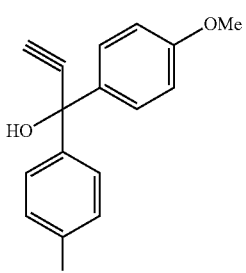 | 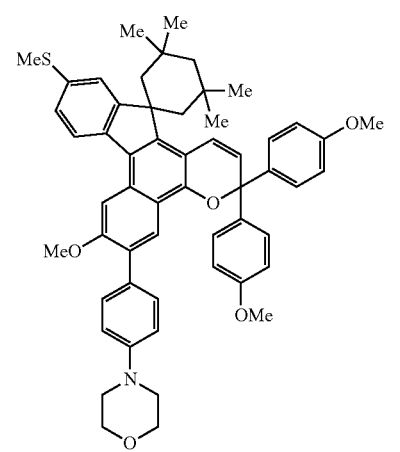 [SMILES: COc1ccc(C2(c3ccc(OC)cc3)C=Cc3c4c(c5cc(OC)c(-c6ccc(N7CCOCC7)cc6)cc5c3O2)-c2ccc(SC)cc2C42CC(C)(C)CC(C)(C)C2)cc1] | 66 |
TABLE 4
| Example No. | Raw materials | | Product | Yield (%) |
|---|---|---|---|---|
| | Naphthol compound | Propargyl alcohol compound | | |
| 11 | 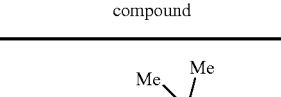 | 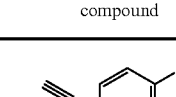 | 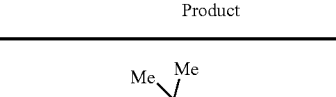 | 61 |

TABLE 4-continued

| Example No. | Raw materials | | Product | Yield (%) |
|---|---|---|---|---|
| | Naphthol compound | Propargyl alcohol compound | | |
| 12 | (structure) | (structure) | (structure) | 72 |
| 13 | (structure) | (structure) | (structure) | 66 |

TABLE 5

| Example No. | Raw materials | | Product | Yield (%) |
|---|---|---|---|---|
| | Naphthol compound | Propargyl alcohol compound | | |
| 14 | (structure) | (structure) | (structure) | 68 |

TABLE 5-continued

| Example No. | Raw materials - Naphthol compound | Raw materials - Propargyl alcohol compound | Product | Yield (%) |
|---|---|---|---|---|
| 15 | (structure) | (structure) | (structure) | 60 |
| 16 | (structure) | (structure) | (structure) | 64 |

TABLE 6

| Example No. | Experimental values C | H | N | S | Calculated values C | H | N | S | $^1$H-NMR(NMR) |
|---|---|---|---|---|---|---|---|---|---|
| 2 | 76.93 | 6.91 | | 3.65 | 76.94 | 6.80 | | 3.67 | δ 5.0-9.0 18H<br>δ 0.5-4.5 41H |
| 3 | 77.71 | 6.73 | | 3.99 | 77.72 | 6.65 | | 3.91 | δ 5.0-9.0 18H<br>δ 0.5-4.5 36H |
| 4 | 81.60 | 6.55 | | 3.99 | 81.65 | 6.48 | | 3.96 | δ 5.0-9.0 22H<br>δ 0.5-4.5 30H |
| 5 | 77.60 | 6.47 | | 4.00 | 77.58 | 6.51 | | 3.98 | δ 5.0-9.0 19H<br>δ 0.5-4.5 33H |
| 6 | 79.30 | 6.82 | | 4.02 | 79.27 | 6.78 | | 3.99 | δ 5.0-9.0 18H<br>δ 0.5-4.5 36H |
| 7 | 78.55 | 7.00 | | 3.67 | 78.52 | 7.04 | | 3.61 | δ 5.0-9.0 18H<br>δ 0.5-4.5 44H |
| 8 | 72.99 | 5.78 | | 3.91 | 72.91 | 5.89 | | 3.67 | δ 5.0-9.0 18H<br>δ 0.5-4.5 33H |
| 9 | 80.81 | 6.77 | | 3.91 | 80.79 | 6.78 | | 4.15 | δ 5.0-9.0 19H<br>δ 0.5-4.5 33H |
| 10 | 78.46 | 6.74 | 1.69 | 3.90 | 78.26 | 6.81 | 1.66 | 3.80 | δ 5.0-9.0 19H<br>δ 0.5-4.5 38H |
| 11 | 78.57 | 6.32 | | 4.38 | 78.58 | 6.46 | | 4.28 | δ 5.0-9.0 18H<br>δ 0.5-4.5 30H |
| 12 | 77.76 | 6.65 | | 3.98 | 77.72 | 6.65 | | 3.91 | δ 5.0-9.0 18H<br>δ 0.5-4.5 36H |
| 13 | 76.81 | 6.03 | 1.70 | 3.89 | 76.69 | 6.19 | 1.69 | 3.86 | δ 5.0-9.0 18H<br>δ 0.5-4.5 33H |

TABLE 6-continued

| Example No. | Elemental analysis values | | | | | | | | $^1$H-NMR(NMR) |
|---|---|---|---|---|---|---|---|---|---|
| | Experimental values | | | | Calculated values | | | | |
| | C | H | N | S | C | H | N | S | |
| 14 | 80.49 | 6.44 | | 3.75 | 80.44 | 6.40 | | 3.77 | δ 5.0-9.0 24H |
| | | | | | | | | | δ 0.5-4.5 30H |
| 15 | 78.50 | 6.37 | | 4.11 | 78.58 | 6.46 | | 4.28 | δ 5.0-9.0 18H |
| | | | | | | | | | δ 0.5-4.5 30H |
| 16 | 78.50 | 6.37 | | 4.11 | 78.58 | 6.46 | | 4.28 | δ 5.0-9.0 20H |
| | | | | | | | | | δ 0.5-4.6 29H |

Synthesis of Chromene Compound

Example 17

1.0 g (2.1 mmol) of the following naphthol compound (25) and 0.80 g (3.0 mmol) of the above propargyl alcohol compound (23) were dissolved in 70 ml of toluene, 0.022 g of p-toluenesulfonic acid was further added to the resulting solution, and the obtained mixture was stirred under reflux by heating for 1 hour.

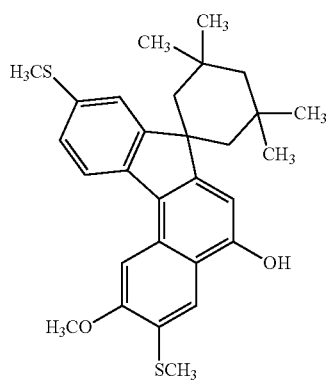

(25)

(23)

After a reaction, the solvent was removed, and the obtained product was purified on silica gel by chromatography to obtain 1.1 g of a white powder product. The yield was 72%.

The elemental analysis values of this product were 75.68%; of C, 6.70%; of H and 8.93%; of S, which were almost equal to the calculated values of $C_{45}H_{46}O_4S$(C, 75.79%; H, 6.64%; S, 8.80%).

When the proton nuclear magnetic resonance spectrum of the product was measured, it showed 18H peaks based on the methyl proton and methylene proton of a tetramethylcyclohexane ring at δ of around 1.0 to 3.0 ppm, 15H peaks based on the methyl proton of a methylthio group and the methyl proton of a methoxy group at δ of around 2.3 to 4.0 ppm and 16H peaks based on an aromatic proton and an alkene proton at δ of around 5.6 to 9.0 ppm.

Further, when the $^{13}$C-nuclear magnetic resonance spectrum was measured, it showed a peak based on the carbon of an aromatic ring at δ of around 110 to 160 ppm, a peak based on the carbon of an alkene at δ of around 80 to 140 ppm and a peak based on the carbon of an alkyl at δ of around 20 to 60 ppm.

It was confirmed from the above results that the isolated product was a compound represented by the following formula (26).

(26)

Synthesis of Chromene Compound

Examples 18 to 32

Chromene compounds shown in Tables 7 to 11 were synthesized in the same manner as in Example 17. When the structures of the obtained products were analyzed by using the same structure confirming means as in Example 1, it was confirmed that they were compounds represented by structural formulas shown in Tables 7 to 11. Table 12 shows the elemental analysis values, calculated values obtained from the structural formulas and characteristic $^1$H-NMR spectra of these compounds.

TABLE 7

| Example No. | Raw materials | | Product | Yield (%) |
|---|---|---|---|---|
| | Naphthol compound | Propargyl alcohol compound | | |
| 18 | | | | 75 |
| 19 | | | | 77 |
| 20 | | | | 73 |

TABLE 8
| Example No. | Raw materials | | Product | Yield (%) |
|---|---|---|---|---|
| | Naphthol compound | Propargyl alcohol compound | | |
| 21 | 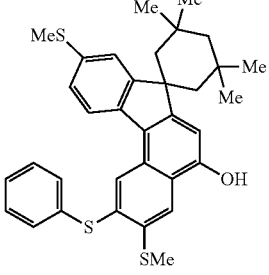 | 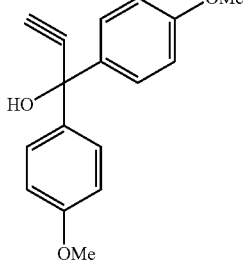 | 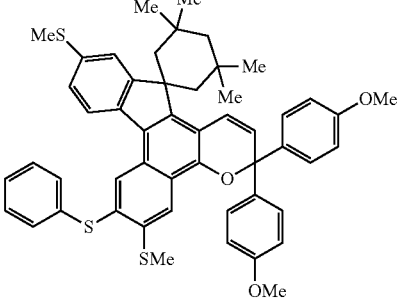 | 68 |
| 22 | 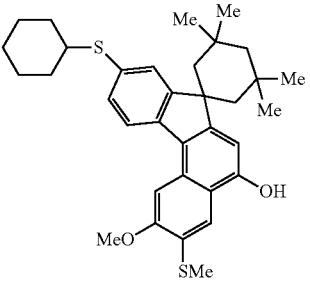 [SMILES: COc1cc2c3c(cc(O)c2cc1SC)C1(CC(C)(C)CC(C)(C)C1)c1cc(SC2CCCCC2)ccc1-3] | 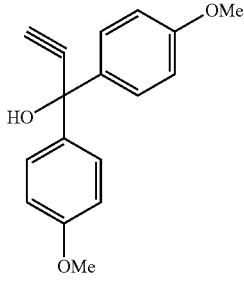 | 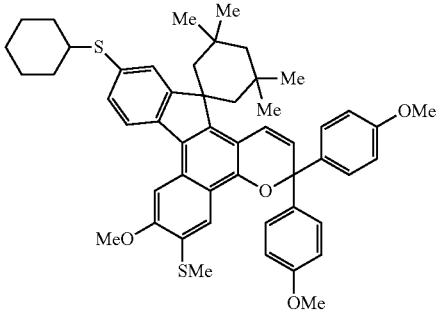 [SMILES: COc1ccc(C2(c3ccc(OC)cc3)C=Cc3c4c(c5cc(OC)c(SC)cc5c3O2)-c2ccc(SC3CCCCC3)cc2C42CC(C)(C)CC(C)(C)C2)cc1] | 67 |
| 23 | 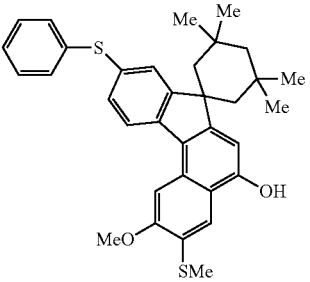 [SMILES: COc1cc2c3c(cc(O)c2cc1SC)C1(CC(C)(C)CC(C)(C)C1)c1cc(Sc2ccccc2)ccc1-3] | 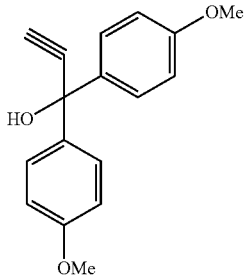 [SMILES: C#CC(O)(c1ccc(OC)cc1)c1ccc(OC)cc1] | 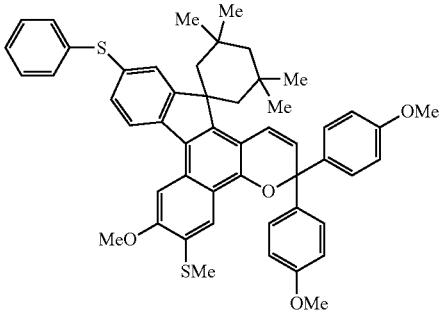 [SMILES: COc1ccc(C2(c3ccc(OC)cc3)C=Cc3c4c(c5cc(OC)c(SC)cc5c3O2)-c2ccc(Sc3ccccc3)cc2C42CC(C)(C)CC(C)(C)C2)cc1] | 69 |

TABLE 9

| Example No. | Raw materials | | Product | Yield (%) |
|---|---|---|---|---|
| | Naphthol compound | Propargyl alcohol compound | | |
| 24 | | | | 64 |
| 25 | | | | 61 |
| 26 | | | | 64 |

TABLE 10

| Example No. | Raw materials | | Product | Yield (%) |
|---|---|---|---|---|
| | Naphthol compound | Propargyl alcohol compound | | |
| 27 | [structure] | [structure] | [structure] | 66 |
| 28 | [structure] | [structure] | [structure] | 62 |
| 29 | [structure] | [structure] | [structure] | 74 |

TABLE 11

| Example No. | Raw materials | | Product | Yield (%) |
| --- | --- | --- | --- | --- |
| | Naphthol compound | Propargyl alcohol compound | | |
| 30 | [structure] | [structure] | [structure] | 72 |
| 31 | [structure] | [structure] | [structure] | 70 |
| 32 | [structure] | [structure] | [structure] | 63 |

TABLE 12

| Example No. | Elemental analysis values | | | | | | | | ¹H-NMR(NMR) |
| --- | --- | --- | --- | --- | --- | --- | --- | --- | --- |
| | Experimental values | | | | Calculated values | | | | |
| | C | H | N | S | C | H | N | S | |
| 18 | 74.21 | 6.55 | | 12.79 | 74.15 | 6.49 | | 12.91 | δ 5.0-9.0 15H<br>δ 0.5-4.5 33H |
| 19 | 75.84 | 6.52 | | 8.93 | 75.79 | 6.64 | | 8.80 | δ 5.0-9.0 15H<br>δ 0.5-4.5 31H |
| 20 | 75.35 | 6.92 | | 11.84 | 75.33 | 6.94 | | 11.83 | δ 5.0-9.0 15H<br>δ 0.5-4.5 41H |

TABLE 12-continued

| Example No. | Elemental analysis values | | | | | | | | $^1$H-NMR(NMR) |
|---|---|---|---|---|---|---|---|---|---|
| | Experimental values | | | | Calculated values | | | | |
| | C | H | N | S | C | H | N | S | |
| 21 | 75.88 | 6.22 | | 11.94 | 75.89 | 6.24 | | 11.92 | δ 5.0-9.0 20H<br>δ 0.5-4.5 30H |
| 22 | 76.88 | 7.03 | | 8.05 | 76.85 | 7.08 | | 8.05 | δ 5.0-9.0 15H<br>δ 0.5-4.5 41H |
| 23 | 77.44 | 6.38 | | 8.13 | 77.43 | 6.37 | | 8.11 | δ 5.0-9.0 20H<br>δ 0.5-4.5 30H |
| 24 | 75.11 | 6.69 | 1.82 | 8.20 | 75.06 | 6.81 | 1.79 | 8.18 | δ 5.0-9.0 15H<br>δ 0.5-4.5 38H |
| 25 | 76.69 | 5.81 | | 8.23 | 76.85 | 5.79 | | 8.19 | δ 5.0-9.0 15H<br>δ 0.5-4.5 30H |
| 26 | 76.91 | 5.89 | | 8.21 | 76.85 | 5.79 | | 8.19 | δ 5.0-9.0 15H<br>δ 0.5-4.5 30H |
| 27 | 74.72 | 6.61 | | 12.28 | 74.57 | 6.78 | | 12.44 | δ 5.0-9.0 15H<br>δ 0.5-4.5 37H |
| 28 | 74.94 | 6.68 | 1.91 | 8.18 | 75.06 | 6.81 | 1.79 | 8.18 | δ 5.0-9.0 15H<br>δ 0.5-4.5 38H |
| 29 | 77.22 | 6.63 | | 9.07 | 77.32 | 6.63 | | 9.17 | δ 5.0-9.0 15H<br>δ 0.5-4.5 31H |
| 30 | 77.44 | 6.87 | | 8.99 | 77.49 | 6.79 | | 8.99 | δ 5.0-9.0 15H<br>δ 0.5-4.5 33H |
| 31 | 74.57 | 6.64 | 1.78 | 8.48 | 74.67 | 6.53 | 1.85 | 8.48 | δ 5.0-9.0 15H<br>δ 0.5-4.5 34H |
| 32 | 74.74 | 7.09 | 3.43 | 7.68 | 74.61 | 7.09 | 3.28 | 7.52 | δ 5.0-9.0 15H<br>δ 0.5-4.5 45H |

Me in the chemical formulas in this text denotes a methyl group and Et denotes an ethyl group.

Use of Chromene Compound

Examples 33 to 64

Evaluation of Physical Properties of Photochromic Plastic Lens Manufactured by Coating Method The chromene compound obtained in Example 1 was mixed with a photopolymerization initiator and polymerizable monomers, the resulting mixture was applied to the surface of a lens substrate, and ultraviolet light was applied to polymerize the coating film on the surface of the lens substrate.

As for the photochromic curable composition, a mixture of 50 parts by mass of 2,2-bis(4-methacryloyloxypentaethoxyphenyl)propane, 10 parts by mass of polyethylene glycol diacrylate (average molecular weight of 532), 10 parts by mass of trimethylolpropane trimethacrylate, 10 parts by mass of polyester oligomer hexaacrylate (ER-1830 of Daicel UCB Co., Ltd.) and 10 parts by mass of glycidyl methacrylate as radically polymerizable monomers was used. After 1 part by mass of the chromene compound obtained in Example 1 was added to and fully mixed with 90 parts by mass of the mixture of these radically polymerizable monomers, 0.3 part by mass of CGI1800 {a mixture of 1-hydroxycyclohexylphenyl ketone and bis(2,6-dimethoxybenzoyl)-2,4,4-trimethyl-pentylphosphine oxide (weight ratio of 3:1)} as a photopolymerization initiator, 5 parts by mass of bis(1,2,2,6,6-pentamethyl-4-piperidyl) sebacate and 3 parts by mass of ethylenebis(oxyethylene)bis[3-(5-tert-butyl-4-hydroxy-m-tolyl) propionate] as a stabilizer, 7 parts by mass of γ-methacryloyloxypropyl trimethoxysilane as a silane coupling agent and 3 parts by mass of N-methyldiethanolamine were added to and fully mixed with the above mixture to obtain a photochromic curable composition.

Subsequently, about 2 g of the photochromic curable composition obtained by the above method was applied to the surface of a lens substrate (CR39: allyl resin plastic lens; refractive index of 1.50) by using the 1H-DX2 spin coater of MIKASA Co., Ltd. This coated lens was irradiated with light from a metal halide lamp having an output of 120 mW/cm$^2$ in a nitrogen gas atmosphere for 3 minutes to manufacture an optical article (photochromic plastic lens) which was covered with a cured polymer film containing the chromene compound dispersed therein (thickness of polymer film: 40 μm).

The following photochromic properties of the obtained photochromic plastic lens were evaluated. The results obtained by using the chromene compound of Example 1 are shown in Table 13.

[1] Maximum absorption wavelength ($\lambda_{max}$): This is the maximum absorption wavelength after color development obtained by means of the spectrophotometer (MCPD3000 instantaneous multi-channel photodetector) of Otsuka Electronics Co., Ltd. and used as an index of color at the time of color development. The maximum absorption wavelength is connected with color at the time of color development.

[2] Color optical density ($A_0$): This is the difference between absorbance {ϵ(120)} after 120 seconds of exposure at the above maximum absorption wavelength and absorbance ϵ(0) under no exposure and used as an index of color optical density. It can be said that as this value becomes larger, photochromic properties become better.

[3] Double peak characteristic ($A_Y/A_B$): This is the ratio of color optical density ($A_Y$: value of $\lambda_{max}$) at a yellow range (having a maximum absorption wavelength at 430 to 530 nm) and color optical density ($A_B$: value of $\lambda_{max}$) at a blue range (having a maximum absorption wavelength at 550 to 650 nm) and used as an index of double peak characteristic. When the double peak characteristic is 0.8 or more to less than 1.1, a gray color is obtained and when the double peak characteristic is 1.1 to 2.0, a brown color is obtained.

[4] Fading half period [τ½ (sec.)]: This is a time required for the reduction of the absorbance at the above maximum absorption wavelength of a sample to ½ of {ε(120)−ε(0)} when exposure is stopped after 120 seconds of exposure and used as an index of fading speed. As this time becomes shorter, the fading speed becomes higher.

[5] Absorption end {$\lambda_0$}: After the photochromic plastic lens obtained under the above conditions is used as a sample and kept in the dark for one day, the ultraviolet light transmittance (T %) at 300 to 800 nm of the sample is measured with an ultraviolet visible spectrophotometer (UV-2550 of Shimadzu Corporation) at room temperature. A tangent line is drawn on the obtained ultraviolet light absorption curve to ensure that the transmittance (T %) of the ultraviolet light absorption curve passes a point of 50% so as to obtain an absorption wavelength at which the transmittance (T %) of the tangent line becomes 0 as the absorption end (absorption end of the ultraviolet light spectrum) and used as an index of initial coloration. For example, in an optical article such as a spectacle lens, as this value becomes smaller, initial coloration becomes weaker and transparency under no exposure becomes higher.

[6] Thermochromism {$T_0$}: The photochromic plastic lens obtained under the above conditions is used as a sample and the transmittance (T %) at 300 to 800 nm of the sample is measured with an ultraviolet visible spectrophotometer (UV-2550 of Shimadzu Corporation) at room temperature. This is a transmittance at a wavelength at which the transmittance at 430 to 650 nm becomes minimal and used as an index of initial coloration. As this value becomes larger, initial coloration becomes weaker and transparency under no exposure becomes higher.

[7] Residual rate ($A_{50}/A_0 \times 100$): A deterioration promotion test is made on the obtained photochromic plastic lens by using the X25 xenon weather meter of Suga Test Instruments Co., Ltd. for 50 hours. Thereafter, the above color optical density is evaluated before and after the test by measuring the color optical density ($A_0$) before the test and the color optical density ($A_{50}$) after the test in order to obtain the ratio ($A_{50}/A_0$) of these values as residual rate which is used as an index of color development durability. As the residual rate becomes higher, color development durability becomes higher.

[8] color development sensitivity [ε(10)/ε(120)]: The photochromic plastic lens obtained under the above conditions is used as a sample to calculate the ratio of color optical density after 120 seconds of exposure {ε(120)} and color optical density after 10 seconds of exposure {ε(10)} as an index of color development sensitivity. As this value becomes larger, the photochromic plastic lens develops a deep color in a shorter period of time upon exposure.

[9] visible light color optical density [$A_0'$]: The photochromic plastic lens obtained under the above conditions is used as a sample. This is the difference between absorbance {ε(120)'} at the above maximum wavelength after 120 seconds of exposure to light passing through an ultraviolet screen filter (L39 of HOYA Corporation) and absorbance ε(0)' under no exposure and used as an index of visible light sensitivity. As this value becomes larger, sensitivity to sunlight becomes higher. Photochromic plastic lenses were obtained and their characteristic properties were evaluated in the same manner as described above except that the chromene compounds obtained in Examples 2 to 32 were used. The results are shown in Tables 13 to 14. In Tables 13 and 14, the compounds Nos. 1 to 32 correspond to the chromene compounds obtained in Example Nos. 1 to 32, respectively. For example, the chromene compound obtained in Example 1 is represented as compound No. 1.

TABLE 13

| Example No. | Chromene compound No.* | λ max (nm) | Color optical density $A_0$ | Double peak characteristic $A_F/A_B$ | Fading half period ½ (sec) | Initial coloration (absorption end) (nm) |
|---|---|---|---|---|---|---|
| 33 | 1 | 460 | 0.67 | 1.31 | 67 | 409 |
|    |   | 578 | 0.51 |      | 67 |     |
| 34 | 2 | 571 | 0.89 | 1.46 | 90 | 415 |
|    |   | 581 | 0.61 |      | 90 |     |
| 35 | 3 | 458 | 0.64 | 1.28 | 68 | 407 |
|    |   | 579 | 0.50 |      | 69 |     |
| 36 | 4 | 456 | 0.57 | 1.12 | 57 | 413 |
|    |   | 575 | 0.51 |      | 57 |     |
| 37 | 5 | 466 | 0.69 | 1.35 | 97 | 415 |
|    |   | 574 | 0.51 |      | 97 |     |
| 38 | 6 | 444 | 0.69 | 1.01 | 51 | 412 |
|    |   | 581 | 0.68 |      | 51 |     |
| 39 | 7 | 456 | 0.56 | 1.12 | 60 | 406 |
|    |   | 575 | 0.50 |      | 60 |     |
| 40 | 8 | 455 | 0.59 | 1.34 | 55 | 415 |
|    |   | 573 | 0.44 |      | 55 |     |
| 41 | 9 | 449 | 0.83 | 1.30 | 81 | 406 |
|    |   | 567 | 0.64 |      | 81 |     |
| 42 | 10 | 467 | 0.71 | 1.27 | 73 | 410 |
|    |    | 584 | 0.56 |      | 73 |     |
| 43 | 11 | 454 | 0.63 | 1.13 | 65 | 408 |
|    |    | 572 | 0.56 |      | 65 |     |
| 44 | 12 | 460 | 0.60 | 1.03 | 70 | 425 |
|    |    | 570 | 0.58 |      | 70 |     |
| 45 | 13 | 458 | 0.56 | 1.22 | 71 | 426 |
|    |    | 572 | 0.46 |      | 71 |     |
| 46 | 14 | 465 | 0.66 | 1.08 | 77 | 430 |
|    |    | 575 | 0.61 |      | 77 |     |
| 47 | 15 | 466 | 0.60 | 1.02 | 61 | 424 |
|    |    | 579 | 0.59 |      | 61 |     |
| 48 | 16 | 479 | 0.75 | 1.00 | 94 | 426 |
|    |    | 588 | 0.75 |      | 94 |     |

TABLE 13-continued

| Example No. | Initial coloration (thermochromism) (%) | Residual rate $(A_{50}/A_0) \times 100$ (%) | Color development sensitivity $\epsilon(10)/\epsilon(120)$ | Visible light color optical density $A_0$ |
|---|---|---|---|---|
| 33 | 89 | 92 | 0.29 | 0.40 |
|    | 89 | 92 |      | 0.31 |
| 34 | 85 | 88 | 0.31 | 0.58 |
|    | 84 | 89 |      | 0.40 |
| 35 | 84 | 93 | 0.29 | 0.40 |
|    | 84 | 93 |      | 0.31 |
| 36 | 90 | 91 | 0.31 | 0.37 |
|    | 90 | 91 |      | 0.33 |
| 37 | 83 | 80 | 0.29 | 0.46 |
|    | 83 | 80 |      | 0.34 |
| 38 | 90 | 91 | 0.32 | 0.43 |
|    | 90 | 91 |      | 0.42 |
| 39 | 90 | 93 | 0.26 | 0.34 |
|    | 90 | 93 |      | 0.31 |
| 40 | 87 | 89 | 0.31 | 0.38 |
|    | 87 | 89 |      | 0.28 |
| 41 | 82 | 85 | 0.29 | 0.50 |
|    | 82 | 85 |      | 0.38 |
| 42 | 83 | 92 | 0.34 | 0.45 |
|    | 83 | 92 |      | 0.35 |
| 43 | 84 | 88 | 0.28 | 0.39 |
|    | 84 | 88 |      | 0.35 |
| 44 | 87 | 88 | 0.37 | 0.44 |
|    | 87 | 88 |      | 0.43 |
| 45 | 85 | 86 | 0.36 | 0.39 |
|    | 85 | 86 |      | 0.32 |
| 46 | 84 | 90 | 0.39 | 0.51 |
|    | 84 | 90 |      | 0.48 |
| 47 | 87 | 88 | 0.35 | 0.44 |
|    | 87 | 88 |      | 0.44 |
| 48 | 81 | 93 | 0.36 | 0.56 |
|    | 81 | 93 |      | 0.56 |

*Chromene compounds Nos. 1 to 16 correspond to Examples 1 to 16, respectively.

TABLE 14

| Example No. | Chromene Compound No.* | λ max (nm) | Color optical density $A_0$ | Double peak characteristic $A_Y/A_B$ | Fading half period 1/2 (sec) | Initial coloration (absorption end) (nm) |
|---|---|---|---|---|---|---|
| 49 | 17 | 473 | 0.55 | 1.53 | 52 | 400 |
|    |    | 580 | 0.36 |      | 52 |     |
| 50 | 18 | 463 | 0.52 | 1.58 | 47 | 411 |
|    |    | 573 | 0.33 |      | 47 |     |
| 51 | 19 | 464 | 0.56 | 1.40 | 47 | 406 |
|    |    | 576 | 0.40 |      | 47 |     |
| 52 | 20 | 467 | 0.61 | 1.49 | 55 | 407 |
|    |    | 571 | 0.41 |      | 55 |     |
| 53 | 21 | 455 | 0.38 | 1.15 | 42 | 407 |
|    |    | 566 | 0.33 |      | 42 |     |
| 54 | 22 | 472 | 0.50 | 1.43 | 48 | 400 |
|    |    | 579 | 0.35 |      | 48 |     |
| 55 | 23 | 473 | 0.45 | 1.32 | 45 | 400 |
|    |    | 580 | 0.34 |      | 45 |     |
| 56 | 24 | 485 | 0.76 | 1.81 | 79 | 414 |
|    |    | 590 | 0.42 |      | 79 |     |
| 57 | 25 | 475 | 0.55 | 1.53 | 41 | 400 |
|    |    | 582 | 0.36 |      | 41 |     |
| 58 | 26 | 466 | 0.52 | 1.58 | 40 | 409 |
|    |    | 576 | 0.33 |      | 40 |     |
| 59 | 27 | 465 | 0.58 | 1.38 | 52 | 406 |
|    |    | 479 | 0.42 |      | 52 |     |
| 60 | 28 | 481 | 0.80 | 1.57 | 83 | 425 |
|    |    | 592 | 0.51 |      | 83 |     |
| 61 | 29 | 456 | 0.66 | 1.61 | 60 | 411 |
|    |    | 564 | 0.41 |      | 60 |     |
| 62 | 30 | 454 | 0.58 | 1.32 | 53 | 407 |
|    |    | 665 | 0.44 |      | 53 |     |
| 63 | 31 | 478 | 0.52 | 1.08 | 50 | 412 |
|    |    | 581 | 0.48 |      | 50 |     |
| 64 | 32 | 488 | 0.66 | 1.25 | 77 | 414 |
|    |    | 592 | 0.53 |      | 77 |     |

| Example No. | Initial coloration (thermochromism) (%) | Residual rate $(A_{50}/A_0) \times 100$ (%) | Color development sensitivity $\epsilon(10)/\epsilon(120)$ | Visible light color optical density $A_0$ |
|---|---|---|---|---|
| 49 | 87 | 86 | 0.27 | 0.32 |
|    | 86 | 86 |      | 0.21 |
| 50 | 88 | 82 | 0.28 | 0.33 |
|    | 88 | 82 |      | 0.21 |
| 51 | 89 | 84 | 0.26 | 0.34 |
|    | 90 | 84 |      | 0.24 |
| 52 | 89 | 84 | 0.29 | 0.38 |
|    | 90 | 84 |      | 0.26 |
| 53 | 90 | 84 | 0.25 | 0.24 |
|    | 90 | 84 |      | 0.21 |
| 54 | 87 | 87 | 0.27 | 0.30 |
|    | 87 | 87 |      | 0.21 |
| 55 | 88 | 87 | 0.26 | 0.27 |
|    | 87 | 88 |      | 0.20 |
| 56 | 85 | 84 | 0.37 | 0.50 |
|    | 85 | 84 |      | 0.28 |
| 57 | 85 | 85 | 0.28 | 0.33 |
|    | 85 | 84 |      | 0.22 |
| 58 | 85 | 82 | 0.30 | 0.33 |
|    | 85 | 82 |      | 0.21 |
| 59 | 88 | 82 | 0.27 | 0.36 |
|    | 88 | 82 |      | 0.26 |

TABLE 14-continued

| | | | | |
|---|---|---|---|---|
| 60 | 84 | 89 | 0.39 | 0.59 |
| | 86 | 89 | | 0.38 |
| 61 | 85 | 81 | 0.29 | 0.41 |
| | 86 | 81 | | 0.25 |
| 62 | 88 | 90 | 0.27 | 0.35 |
| | 88 | 90 | | 0.27 |
| 63 | 89 | 88 | 0.28 | 0.34 |
| | 89 | 88 | | 0.31 |
| 64 | 86 | 87 | 0.36 | 0.43 |
| | 86 | 87 | | 0.34 |

*Chromene compounds No. 17 to 32 correspond to Examples 17 to 32, respectively.

Comparative Examples 1 to 6

For comparison, photochromic plastic lenses were obtained and their characteristic properties were evaluated in the same manner as in Examples except that compounds represented by the following formulas (A) to (G) were used. The results are shown in Table 15.

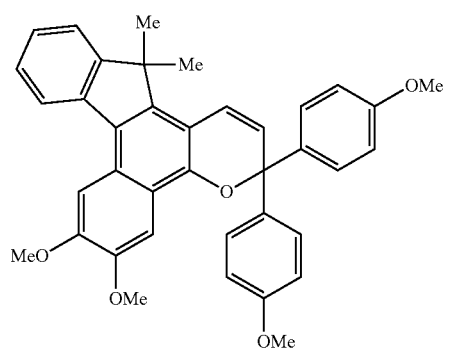

(A)

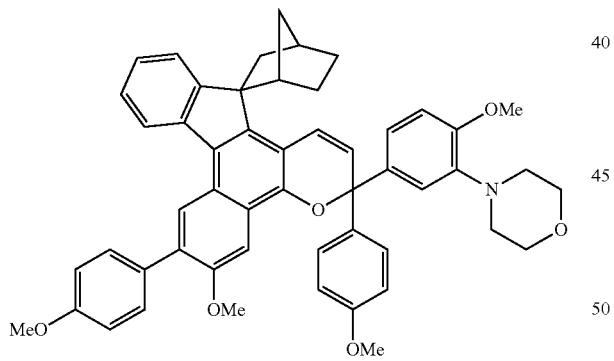

(B)

(C)

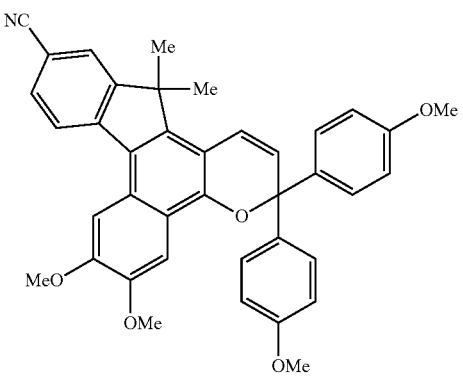

(D)

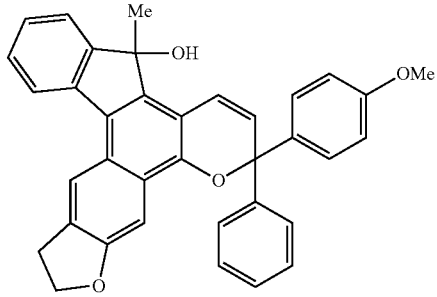

(E)

(G)

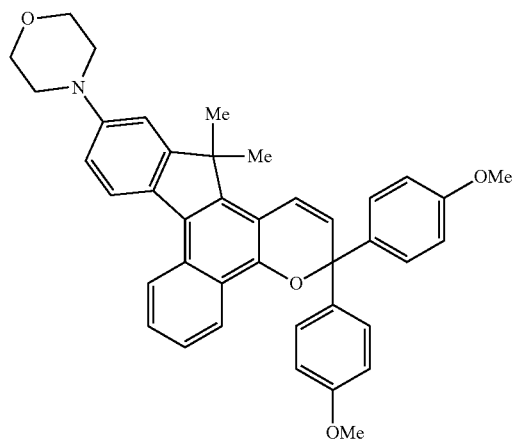

TABLE 15

| Comparative Example No. | Compound No.* | λ max (nm) | Color optical density $A_0$ | Double peak characteristic $A_Y/A_B$ | Fading half period 1/2 (sec) | Initial coloration (absorption end) (nm) |
|---|---|---|---|---|---|---|
| 1 | (A) | 457 | 0.69 | 1.56 | 195 | 397 |
|   |   | 574 | 0.45 |   | 196 |   |
| 2 | (B) | 458 | 0.44 | 1.20 | 68 | 422 |
|   |   | 568 | 0.37 |   | 68 |   |
| 3 | (C) | 461 | 0.38 | 1.58 | 98 | 401 |
|   |   | 579 | 0.24 |   | 98 |   |
| 4 | (D) | 457 | 0.21 | 1.62 | 61 | 402 |
|   |   | 574 | 0.13 |   | 61 |   |
| 5 | (E) | 455 | 0.30 | 0.94 | 83 | 410 |
|   |   | 576 | 0.32 |   | 83 |   |
| 6 | (G) | 457 | 0.40 | 0.63 | 156 | 405 |
|   |   | 570 | 0.63 |   | 156 |   |

| Comparative Example No. | Initial coloration (thermochromism) (%) | Residual rate ($A_{50}/A_0$) × 100 (%) | Color development sensitivity $\epsilon(10)/\epsilon(120)$ | Visible light color optical density $A_0$ |
|---|---|---|---|---|
| 1 | 67 | 76 | 0.22 | 0.24 |
|   | 75 | 77 |   | 0.16 |
| 2 | 84 | 85 | 0.31 | 0.22 |
|   | 86 | 84 |   | 0.19 |
| 3 | 74 | 72 | 0.24 | 0.17 |
|   | 77 | 72 |   | 0.11 |
| 4 | 72 | 72 | 0.24 | 0.10 |
|   | 72 | 74 |   | 0.06 |
| 5 | 77 | 35 | 0.26 | 0.15 |
|   | 78 | 35 |   | 0.16 |
| 6 | 77 | 83 | 0.24 | 0.25 |
|   | 78 | 83 |   | 0.39 |

In the chromene compound of the present invention, the absorption end for obtaining high transparency is preferably at 400 to 420 nm, more preferably at 405 to 420 nm, particularly preferably at 405 to 415 nm from the viewpoints of initial coloration and color development sensitivity. Meanwhile, the absorption end for obtaining high color development sensitivity is preferably at 400 nm or more, particularly preferably at 420 nm or more.

It is understood that Examples 33 to 64 (compounds 1 to 32) comprising the chromene compound of the present invention rarely experience the reduction of color optical density though they have high fading speed and have high repeat durability and high color development sensitivity as well as high double peak characteristic. It is also understood that a chromene compound having an absorption end at 420 nm or more out of the chromene compounds of the present invention has extremely high color optical density for visible light.

Examples of the naphthol compound are given below.

Synthesis of Naphthol Compound

Example 65

90.0 g (381.8 mmol) of a benzene compound represented by the above formula (8) was dissolved in 450 ml of dichloromethane and cooled to 0° C. 148.8 g (1145.4 mmol) of oxalyl chloride and 4 ml of N,N-dimethylformamide were added dropwise to this solution. After addition, the resulting mixture was heated to 25° C. and stirred for 2 hours. After a reaction, the solvent and an excess of oxalyl chloride were distilled off under reduced pressure. The obtained residue was dissolved in 450 ml of tetrahydrofuran and cooled to −50° C. 172 ml (343.6 mmol) of phenylmagnesium bromide (2.0M diethyl ether solution) was added dropwise to this solution. After addition, the resulting mixture was heated to 25° C. and stirred for 4 hours. After a reaction, 200 ml of toluene was added, the reaction solution was washed with water, the solvent was removed, and the obtained product was purified by reslurrying with methanol to obtain a benzophenone derivative represented by the following formula (27) as 73.3 g (214.5 mmol, yield of 56%) of a white solid.

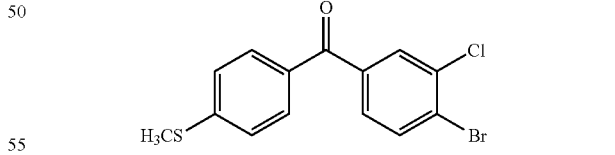

(27)

The benzophenone derivative of the above formula (27) and 67.7 g (372.1 mmol) of 2,4-dimethoxyphenylboronic acid were dissolved in 370 ml of 1,2-dimethoxyethane, and 37 ml of ethanol and 790 ml of a 10% sodium carbonate aqueous solute were added. After this solution was deaerated in a nitrogen gas stream, 0.287 g (0.248 mmol) of tetrakis(triphenylphosphine)palladium was added and refluxed for 3 hours. After a reaction, 400 ml of toluene was added, the reaction solution was washed with water, the solvent was removed, and the obtained product was purified by reslurrying with methanol to obtain a compound represented by the following formula (28) as 83.9 g (210.2 mmol, yield of 98%) of a white solid.

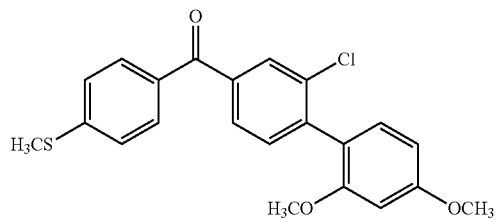

(28)

The compound of the above formula (28), 93.4 g (972.4 mmol) of sodium-t-butoxide, 5.5 g (24.3 mmol) of palladium acetate, 14.7 g (72.9 mmol) of tri-t-butylphosphine and 63.6 g (729.3 mmol) of morpholine were dissolved in 920 ml of toluene and refluxed for 3 hours in an argon atmosphere. After a reaction, the reaction solution was washed with water, the solvent was removed, and the obtained product was purified with reslurrying with methanol to obtain a compound represented by the following formula (29) as 60.8 g (135.2 mmol, yield of 64%) of a white solid.

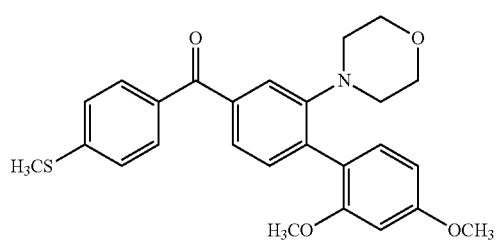

(29)

The compound of the above formula (29) and 30.2 g (173.3 mmol) of diethyl succinate were dissolved in 200 ml of tetrahydrofuran and heated to 55° C. A tetrahydrofuran solution (425 ml) containing 19.4 g (173.3 mmol) of potassium-t-butoxide was added dropwise to this solution and stirred for 1 hour. After a reaction, 200 ml of toluene was added, the reaction solution was washed with concentrated hydrochloric acid and then with water, and the solvent was removed to obtain a compound represented by the following formula (30) as 77.1 g (128.1 mmol, yield of 95%) of orange oil.

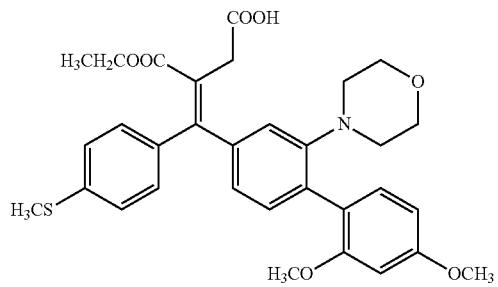

(30)

The compound of the above formula (30), 12.4 g (150.7 mmol) of sodium acetate and 76.9 g (750.4 mmol) of acetic anhydride were dissolved in 200 ml of toluene and refluxed for 3 hours. After a reaction, the reaction solution was washed with water, the solvent was removed, and the obtained product was purified by recrystallization with ethyl acetate and acetonitrile so as to obtain a compound represented by the following formula (31) as 18.4 g (30.6 mmol, yield of 24%) of an orange solid.

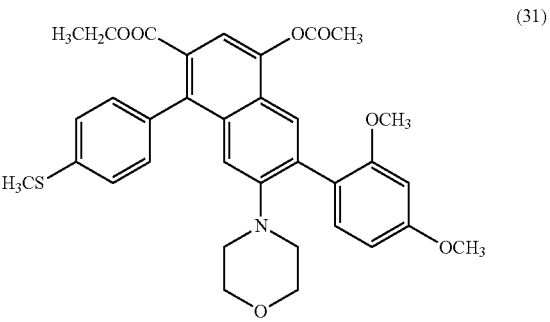

(31)

The compound of the above formula (31) was dispersed into 75 ml of methanol. 80 ml of an aqueous solution containing 8.0 g (199.2 mmol) of sodium hydroxide was added to this solution and refluxed for 3 hours. After a reaction, the reaction solution was washed with concentrated hydrochloric acid and then with water, the solvent was removed, and the obtained product was purified by reslurrying with toluene to obtain a carboxylic acid derivative represented by the following formula (32) as 15.1 g (28.4 mmol, yield of 93%) of a yellow solid.

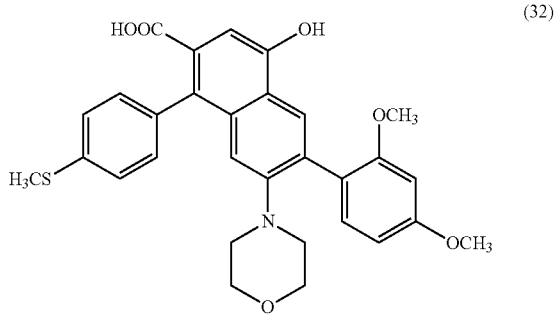

(32)

The carboxylic acid derivative of the above formula (32) and 8.7 g (68.6 mmol) of benzyl chloride were dissolved in 150 ml of N,N-dimethylformamide. 10.8 g (78.0 mmol) of potassium carbonate was added to this solution, and the resulting mixture was heated to 60° C. and stirred for 3 hours. After a reaction, 200 ml of toluene was added, the reaction solution was washed with water, and the solvent was removed to obtain a compound represented by the following formula (33) as 20.3 g (28.5 mmol, yield of 100%) of a yellow solid.

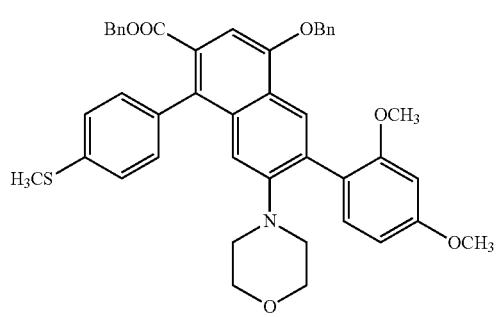

(33)

The compound of the above formula (33) was dispersed into 200 ml of isopropyl alcohol. 184 ml of an aqueous solution containing 36.7 g (918.0 mmol) of sodium hydroxide was added to this solution and refluxed for 3 hours. After a reaction, 300 ml of ethyl acetate was added, the reaction solution was washed with concentrated hydrochloric acid and then with water, the solvent was removed, and the obtained product was purified by reslurrying with toluene to obtain a carboxylic acid derivative represented by the following formula (34) as 17.2 g (27.7 mmol, yield of 97%) of a yellow solid.

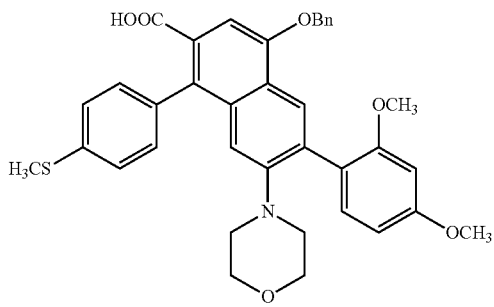

(34)

The carboxylic acid derivative of the above formula (34) was dispersed into 180 ml of toluene. 9.1 g (90.0 mmol) of triethylamine and 10.7 g (39.0 mmol) of diphenylphosphorylazide were added to this solution and stirred at room temperature for 2 hours. 6.9 g (150.0 mmol) of ethanol was added to this solution to carry out a reaction at 70° C. for 2 hours. 86 ml of ethanol was added to this solution, and then 16.8 g (300.0 mmol) of potassium hydroxide was added and refluxed for 3 hours. After a reaction, ethanol was distilled off at normal pressure, tetrahydrofuran was added, the reaction solution was washed with water, and the solvent was removed to obtain a compound represented by the following formula (35) as 14.4 g (24.3 mmol, yield of 88%) of a yellow solid.

(35)

The compound of the above formula (35) was dispersed into 150 ml of acetonitrile, and 113.3 g (130.7 mmol) of a 6% hydrochloric acid aqueous solution was added and cooled to 0 to 5° C. 8.2 g (39.6 mmol) of a 33% sodium nitrite aqueous solution was added to this solution and stirred for 30 minutes. 21.9 g (132.0 mmol) of a 50% potassium iodide aqueous solution was added to this solution and stirred at room temperature for 6 hours. After a reaction, toluene was added, the reaction solution was washed with water, the solvent was removed, and the obtained product was purified by column chromatography to obtain a compound represented by the following formula (36) as 12.5 g (17.8 mmol, yield of 73%) of a yellow solid.

(36)

The compound of the above formula (36) was dispersed into 375 ml of toluene and cooled to −50° C. 13.1 ml (20.9 mmol) of n-butyl lithium (1.6 M hexane solution) was added dropwise to this solution and stirred for 30 minutes. 7.3 g of a toluene solution containing 3.7 g (23.8 mmol) of 3,3,5,5-tetramethylcyclohexanone was added dropwise to this solution and stirred at 0° C. for 3 hours. After a reaction, toluene was added, the reaction solution was washed with water, the solvent was removed, and the obtained product was purified by reslurrying with methanol to obtain a compound represented by the following formula (37) as 7.5 g (10.2 mmol, yield of 57%) of a yellow solid.

(37)

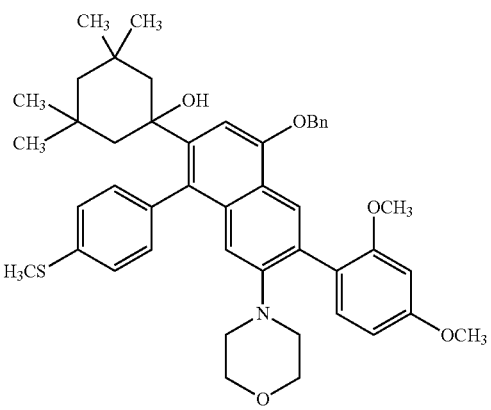

The compound of the above formula (37) was dissolved in 150 ml of tetrahydrofuran, and 2.8 g (44.0 mmol) of ammonium formate and 2.3 g of 5% palladium carbide were added to the resulting solution and stirred at room temperature for 8 hours. After a reaction, 50 ml of toluene was added, the reaction solution was washed with water, the solvent was removed, and the obtained product was purified by reslurrying with toluene to obtain a compound represented by the following formula (38) as 6.0 g (9.3 mmol, yield of 92%) of a yellow solid.

(38)

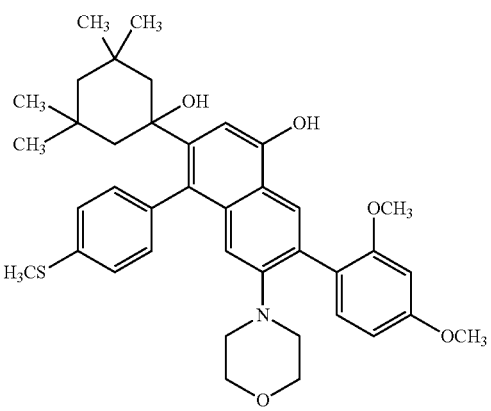

The compound of the above formula (38) was dissolved in 120 ml of toluene and heated to 90° C. 57.6 g (303.0 mmol) of p-toluenesulfonic acid monohydrate was added to this solution and refluxed for 4 hours. After a reaction, the reaction product was washed with water, the solvent was removed, and the obtained product was purified by column chromatography to obtain a naphthol compound represented by the following formula (39) as 4.4 g (7.1 mmol, yield of 76%) of a white solid.

(39)

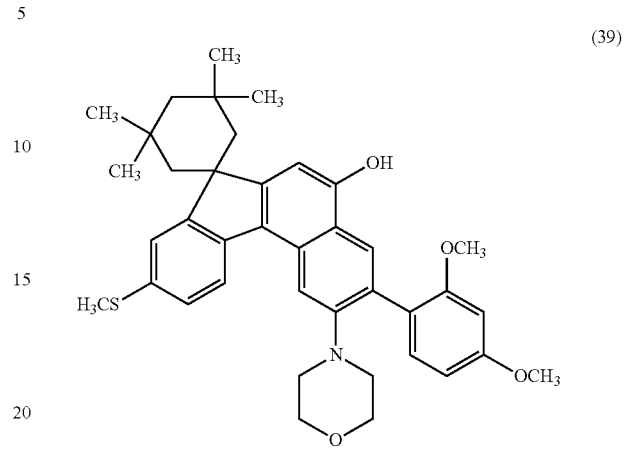

The elemental analysis values of this product were 75.02%; of C, 7.19%; of H, 2.18%; of N and 5.13%; of S, which were almost equal to the calculated values of $C_{38}H_{43}NO_4$ (C, 75.09%; H, 7.27%; N, 2.25%; S, 5.14%).

When the proton nuclear magnetic resonance spectrum of the product was measured, it showed a 35H peak based on an alkyl group at δ of around 0.5 to 4.5 ppm and 10H peaks based on a hydroxyl group and an aromatic proton at δ of around 5.0 to 9.0 ppm.

Further, when the $^{13}$C-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from these results that the isolated product was a compound represented by the above formula (39). This compound is a naphthol compound used in the above Example 2.

Examples 66 to 80

The compound of Example 1 (naphthol compound of the above formula (22)) and naphthol compounds shown in Tables 1 to 5 were synthesized in the same manner as in Example 65. When the structures of the obtained products were analyzed by using the same structure confirming means as in Example 65, it was confirmed that they were the compound of Example 1 (naphthol compound of the above formula (22)) and the naphthol compounds used in Examples shown in Tables 1 to 5. Table 16 shows the elemental analysis values, calculated values obtained from the structural formulas and characteristic $^1$H-NMR spectra of these compounds.

TABLE 16

| Example No. | Chromene compound No. | Experimental values | | | | Calculated values | | | | $^1$H-NMR(NMR) |
|---|---|---|---|---|---|---|---|---|---|---|
| | | C | H | N | S | C | H | N | S | |
| 66 | 1 | 76.84 | 7.29 | | 5.38 | 76.86 | 7.30 | | 5.40 | δ 5.0-9.0 11H |
| | | | | | | | | | | δ 0.5-4.5 32H |
| 67 | 3 | 75.98 | 7.13 | | 5.68 | 76.02 | 7.09 | | 5.64 | δ 5.0-9.0 10H |
| | | | | | | | | | | δ 0.5-4.5 30H |

TABLE 16-continued

| Example No. | Chromene compound No. | Experimental values C | H | N | S | Calculated values C | H | N | S | ¹H-NMR(NMR) |
|---|---|---|---|---|---|---|---|---|---|---|
| 68 | 4 | 81.66 | 6.82 | | 5.74 | 81.68 | 6.85 | | 5.74 | δ 5.0-9.0 14H<br>δ 0.5-4.5 24H |
| 69 | 5 | 75.77 | 6.98 | | 5.76 | 75.78 | 6.90 | | 5.78 | δ 5.0-9.0 10H<br>δ 0.5-4.5 28H |
| 70 | 6 | 78.24 | 7.26 | | 5.77 | 78.22 | 7.29 | | 5.80 | δ 5.0-9.0 10H<br>δ 0.5-4.5 30H |
| 71 | 7 | 77.35 | 7.55 | | 5.05 | 77.32 | 7.60 | | 5.03 | δ 5.0-9.0 10H<br>δ 0.5-4.5 38H |
| 72 | 8 | 69.54 | 6.03 | | 5.24 | 69.43 | 5.99 | | 5.15 | δ 5.0-9.0 10H<br>δ 0.5-4.5 27H |
| 73 | 9 | 77.91 | 7.02 | | 5.81 | 78.03 | 7.11 | | 5.95 | δ 5.0-9.0 11H<br>δ 0.5-4.5 27H |
| 74 | 10 | 76.96 | 7.41 | 2.30 | 5.30 | 76.86 | 7.30 | 2.36 | 5.40 | δ 5.0-9.0 11H<br>δ 0.5-4.5 32H |
| 75 | 11 | 77.14 | 6.84 | | 6.52 | 77.07 | 6.87 | | 6.43 | δ 5.0-9.0 10H<br>δ 0.5-4.5 24H |
| 76 | 12 | 75.85 | 7.09 | | 5.52 | 76.02 | 7.09 | | 5.64 | δ 5.0-9.0 10H<br>δ 0.5-4.5 30H |
| 77 | 13 | 77.59 | 6.15 | | 6.40 | 77.70 | 6.11 | | 6.48 | δ 5.0-9.0 11H<br>δ 0.5-4.5 19H |
| 78 | 14 | 80.01 | 6.71 | | 5.16 | 79.96 | 6.71 | | 5.34 | δ 5.0-9.0 16H<br>δ 0.5-4.5 24H |
| 79 | 15 | 77.10 | 7.06 | | 6.32 | 77.07 | 6.87 | | 6.43 | δ 5.0-9.0 10H<br>δ 0.5-4.5 24H |
| 80 | 16 | 77.75 | 6.91 | | 6.17 | 77.61 | 6.71 | | 6.28 | δ 5.0-9.0 11H<br>δ 0.5-4.5 23H |

*Chromene compound No. (Example No.) denotes chromene compound No. obtained from the naphthol compound of each Example.

Synthesis of Naphthol Compound

Example 81

55.1 g (324.2 mmol) of a benzene compound represented by the above formula (19) was added dropwise to a dichloromethane solution (350 ml) containing 51.8 g (388.6 mmol) of aluminum chloride and 60.5 g (324.3 mmol) of benzoyl chloride cooled to 0° C. After addition, the resulting mixture was stirred for 2 hours. After a reaction, the reaction product was washed with water, the solvent was removed, and the obtained product was purified by column chromatography to obtain a benzophenone derivative represented by the following formula (40) as 63.1 g (196.9 mmol, yield of 61%) of a yellow solid.

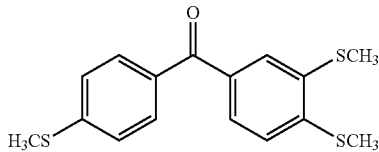
(40)

The benzophenone derivative of the above formula (40) and 46.2 g (265.0 mmol) of diethyl succinate were dissolved in 250 ml of tetrahydrofuran and heated to 55° C. A tetrahydrofuran solution (250 ml) containing 29.7 g (265.0 mmol) of potassium-t-butoxide was added dropwise to this solution and stirred for 1 hour. After a reaction, the reaction solution was washed with concentrated hydrochloric acid and then with water, and the solvent was removed to obtain a compound represented by the following formula (41) as 92.6 g (206.4 mmol, yield of 100%) of orange oil.

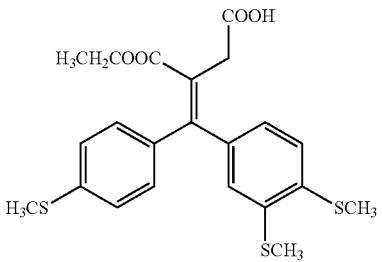
(41)

The compound of the above formula (41), 18.9 g (230.4 mmol) of sodium acetate and 118.7 g (1152.0 mmol) of acetic anhydride were dissolved in 300 ml of toluene and refluxed for 3 hours. After a reaction, the reaction solution was washed with water, the solvent was removed, and the obtained product was purified by recrystallization with methanol so as to obtain a compound represented by the following formula (42) as 22.6 g (47.8 mmol, yield of 23%) of an orange solid.

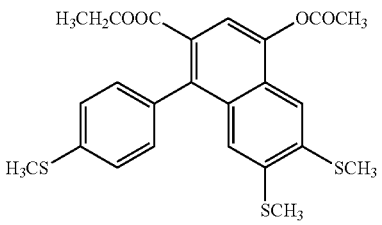
(42)

The compound of the above formula (42) was dispersed into 100 ml of methanol. 127 ml of an aqueous solution containing 12.7 g (318.0 mmol) of sodium hydroxide was added to this solution and refluxed for 3 hours. After a reaction, the reaction solution was washed with concentrated hydrochloric acid and then with water, the solvent was removed, and the obtained product was purified by reslurrying with toluene to obtain a carboxylic acid derivative represented by the following formula (43) as 17.4 g (40.9 mmol, yield of 86%) of a yellow solid.

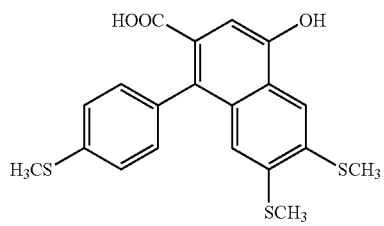

(43)

The carboxylic acid derivative of the above formula (43) and 14.8 g (107.4 mmol) of benzyl chloride were dissolved in 150 ml of N,N-dimethylformamide. 15.4 g (122.0 mmol) of potassium carbonate was added to this solution, and the resulting mixture was heated at 60° C. and stirred for 3 hours. After a reaction, the reaction solution was washed with water, and the solvent was removed to obtain a compound represented by the following formula (44) as 24.1 g (41.4 mmol, yield of 100%) of yellow oil.

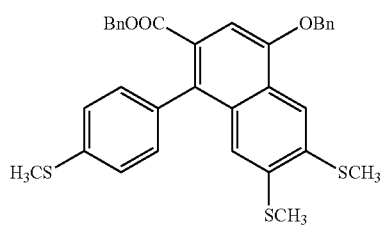

(44)

The compound of the above formula (44) was dispersed into 400 ml of isopropyl alcohol. 150 ml of an aqueous solution containing 30.0 g (750.0 mmol) of sodium hydroxide was added to this solution and refluxed for 3 hours. After a reaction, the reaction solution was washed with concentrated hydrochloric acid and then with water, the solvent was removed, and the obtained product was purified by reslurrying with toluene to obtain a carboxylic acid derivative represented by the following formula (45) as 19.9 g (40.3 mmol, yield of 97%) of a yellow solid.

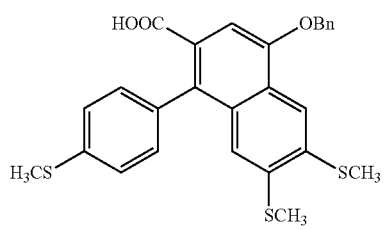

(45)

The carboxylic acid derivative of the above formula (45) was dispersed into 300 ml of toluene. 90.0 g (891.1 mmol) of triethylamine and 15.9 g (57.9 mmol) of diphenylphosphorylazide were added to this solution and stirred at room temperature for 2 hours. 20.0 g (435.3 mmol) of ethanol was added to this solution to carryout a reaction at 70° C. for 2 hours. 500 ml of ethanol was added to this solution, and then 74.7 g (1335.0 mmol) of potassium hydroxide was added and refluxed for 6 hours. After a reaction, ethanol was distilled off at normal pressure, tetrahydrofuran was added, the reaction solution was washed with water, and the solvent was removed to obtain a compound represented by the following formula (46) as 15.8 g (34.1 mmol, yield of 85%) of a yellow solid.

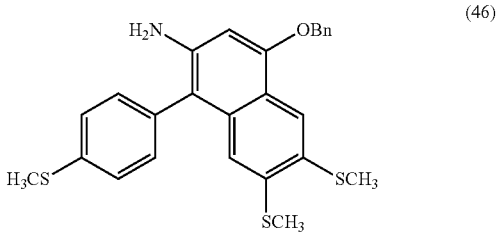

(46)

The compound of the above formula (46) was dispersed into 350 ml of acetonitrile, and 13.7 g (187.1 mmol) of a 6% hydrochloric acid aqueous solution was added and cooled to 0 to 5° C. 11.7 g (56.7 mmol) of a 33% sodium nitrite aqueous solution was added to this solution and stirred for 30 minutes. 47.1 g (283.5 mmol) of a 50% potassium iodide aqueous solution was added to this solution and stirred at room temperature for 5 hours. After a reaction, toluene was added, the reaction solution was washed with water, the solvent was removed, and the obtained product was purified by column chromatography to obtain a compound represented by the following formula (47) as 15.8 g (27.5 mmol, yield of 81%) of a yellow solid.

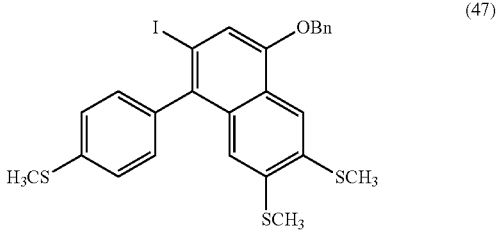

(47)

The compound of the above formula (47) was dispersed into 600 ml of toluene and cooled to −30° C. 28.1 ml (44.9 mmol) of n-butyl lithium (1.6 M hexane solution) was added dropwise to this solution and stirred for 30 minutes. 14.8 g of a toluene solution containing 7.4 g (47.8 mmol) of 3,3,5,5-tetramethylcyclohexanone was added dropwise to this solution and stirred at 0° C. for 3 hours. After a reaction, toluene was added, the reaction solution was washed with water, the solvent was removed, and the obtained product was purified by reslurrying with methanol to obtain a compound represented by the following formula (48) as 10.1 g (16.8 mmol, yield of 61%) of a yellow solid.

(48)

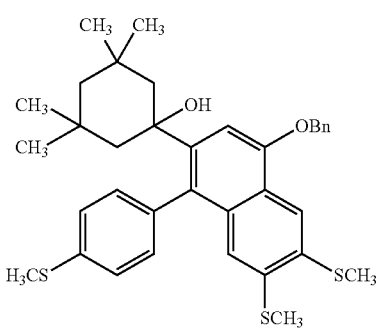

The compound of the above formula (48) and 221.1 mg (0.9 mmol) of (±)-10-camphorsulfonic acid were dissolved in 150 ml of toluene and refluxed for 30 minutes. After the obtained solution was left to be cooled to room temperature, this solution was added to 100 ml of a toluene solution containing 4.5 g (27.3 mmol) of p-toluenesulfonic acid heated at 90° C. and refluxed for 4 hours. After a reaction, the reaction solution was washed with water, the solvent was removed, and the obtained product was purified by column chromatography to obtain a naphthol compound represented by the following formula (49) as 3.7 g (8.2 mmol, yield of 45%) of a yellow solid.

(49)

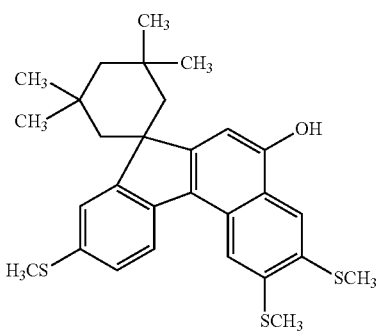

The elemental analysis values of this product were 70.32%; of C, 6.80%; of H, and 19.37%; of S, which were almost equal to the calculated values of $C_{28}H_{32}OS_2$ (C, 70.40%; H, 6.93%; S, 19.44%).

When the proton nuclear magnetic resonance spectrum of the product was measured, it showed a 26H peak based on an alkyl group at δ of around 0.5 to 4.5 ppm and a 7H peak based on an aromatic proton at δ of around 5.0 to 9.0 ppm.

Further, when the $^{13}C$-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from these results that the isolated product was a compound represented by the above formula (49).

This compound is a naphthol compound used in the above Example 19.

Synthesis of Naphthol Compound

Example 82

When the operation of Example 81 was repeated by using 50.0 g (324.6 mmol) of a benzene compound represented by the above formula (18a), a naphthol compound represented by the following formula (50) was obtained as 4.0 g (8.4 mmol, yield of 2.6%) of a yellow solid.

(50)

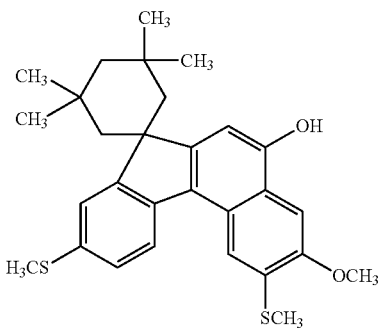

The elemental analysis values of this product were 72.69%; of C, 7.11%; of H and 13.29%; of S, which were almost equal to the calculated values of $C_{28}H_{32}O_2S$ (C, 72.76%; H, 7.16%; S, 13.40%).

When the proton nuclear magnetic resonance spectrum of the product was measured, it showed a 26H peak based on an alkyl group at δ of around 0.5 to 4.5 ppm and a 7H peak based on an aromatic proton at δ of around 5.0 to 9.0 ppm.

Further, when the $^{13}C$-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from the above results that the isolated product was a compound represented by the above formula (48). This compound is a naphthol compound used in the above Example 18.

Synthesis of Naphthol Compound

Example 83

When the operation of Example 81 was repeated by using 55.0 g (348.1 mmol) of a benzene compound represented by the above formula (18b), a benzophenone derivative represented by the following formula (51) was obtained as 63.8 g (206.6 mmol, yield of 59%) of a yellow solid.

(51)

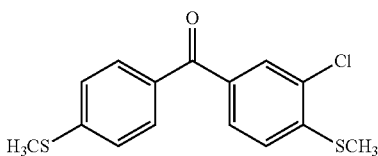

The benzophenone derivative of the above formula (49), 46.8 g (487.4 mmol) of sodium-t-butoxide, 4.5 g (4.9 mmol) of tris(dibenzylideneacetone)dipalladium, 3.5 g (7.3 mmol) of 1,1'-bis(di-t-butylphosphino)ferrocene and 31.8 g (365.5 mmol) of morpholine were dissolved in 650 ml of toluene and refluxed for 3 hours in an argon atmosphere. After a reaction, the reaction solution was washed with water, the solvent was removed, and the obtained product was purified by column chromatography to obtain a benzophenone derivative represented by the following formula (52) as 47.3 g (131.6 mmol, yield of 64%) of a yellow solid.

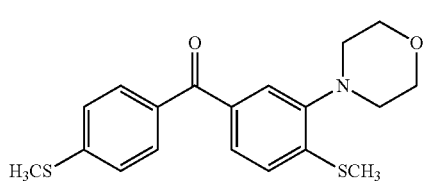

(52)

When the operation of Example 46 was repeated by using the benzophenone derivative represented by the above formula (52), a naphthol compound represented by the following formula (53) was obtained as 4.2 g (7.9 mmol, yield of 6.0%) of a yellow solid.

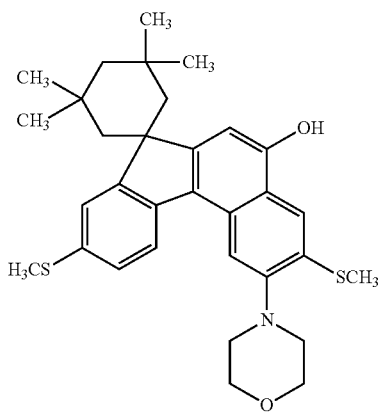

(53)

The elemental analysis values of this product were 71.90%; of C, 7.22%; of H and 11.91%; of S, which were almost equal to the calculated values of $C_{32}H_{39}NO_2S_2$ (C, 72.00%; H, 7.36%; S, 12.01%).

When the proton nuclear magnetic resonance spectrum of the product was measured, it showed a 23H peak based on an alkyl group at δ of around 0.5 to 4.5 ppm and a 7H peak based on an aromatic proton at δ of around 5.0 to 9.0 ppm.

Further, when the $^{13}C$-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from the above results that the isolated product was a compound represented by the above formula (51). This compound is a naphthol compound used in the above Example 24.

Synthesis of Naphthol Compound

Examples 84 to 96

The compound of Example 17 (naphthol compound of the above formula (25)) and naphthol compounds shown in Tables 7 to 11 were synthesized in the same manner as in Examples 81 to 83. When the structures of the obtained products were analyzed by using the same structure confirming means, it was confirmed that they were the compound of Example 17 (naphthol compound of the above formula (25)) and the naphthol compounds used in Examples shown in Tables 7 to 11. Table 17 shows the elemental analysis values, calculated values obtained from the structural formulas and characteristic $^1H$-NMR spectra of these compounds.

TABLE 17

| Example No. | Chromene compound No. | Elemental analysis values | | | | | | | | $^1$H-NMR(NMR) |
|---|---|---|---|---|---|---|---|---|---|---|
| | | Experimental values | | | | Calculated values | | | | |
| | | C | H | N | S | C | H | N | S | |
| 84 | 17 | 72.77 | 7.13 | | 13.37 | 72.76 | 7.16 | | 13.4 | δ 5.0-9.0 7H<br>δ 0.5-4.5 27H |
| 85 | 20 | 72.58 | 7.55 | | 17.03 | 72.55 | 7.52 | | 17.09 | δ 5.0-9.0 7H<br>δ 0.5-4.5 35H |
| 86 | 21 | 73.33 | 6.49 | | 17.25 | 73.34 | 6.52 | | 17.28 | δ 5.0-9.0 12H<br>δ 0.5-4.5 24H |
| 87 | 22 | 74.66 | 7.75 | | 11.75 | 74.68 | 7.74 | | 11.73 | δ 5.0-9.0 7H<br>δ 0.5-4.5 35H |
| 88 | 23 | 75.5 | 6.68 | | 11.88 | 75.51 | 6.71 | | 11.86 | δ 5.0-9.0 12H<br>δ 0.5-4.5 24H |
| 89 | 25 | 65.81 | 5.79 | | 12.12 | 65.87 | 5.87 | | 12.04 | δ 5.0-9.0 7H<br>δ 0.5-4.5 24H |
| 90 | 26 | 65.94 | 5.82 | | 11.99 | 65.87 | 5.87 | | 12.04 | δ 5.0-9.0 7H<br>δ 0.5-4.5 24H |
| 91 | 27 | 71.39 | 7.13 | | 18.39 | 71.21 | 7.33 | | 18.40 | δ 5.0-9.0 7H<br>δ 0.5-4.5 31H |
| 92 | 28 | 71.94 | 7.41 | 2.54 | 11.89 | 72.00 | 7.36 | 2.62 | 12.01 | δ 5.0-9.0 7H<br>δ 0.5-4.5 32H |
| 93 | 29 | 72.32 | 7.00 | | 13.84 | 72.37 | 6.94 | | 13.80 | δ 5.0-9.0 7H<br>δ 0.5-4.5 25H |
| 94 | 30 | 75.46 | 7.51 | | 13.72 | 75.28 | 7.41 | | 13.86 | δ 5.0-9.0 7H<br>δ 0.5-4.5 27H |
| 95 | 31 | 71.88 | 6.80 | | 14.13 | 71.96 | 6.71 | | 14.23 | δ 5.0-9.0 7H<br>δ 0.5-4.5 30H |

TABLE 17-continued

| Example No. | Chromene compound No. | Elemental analysis values | | | | | | | | $^1$H-NMR(NMR) |
|---|---|---|---|---|---|---|---|---|---|---|
| | | Experimental values | | | | Calculated values | | | | |
| | | C | H | N | S | C | H | N | S | |
| 96 | 32 | 72.21 | 7.46 | 2.56 | 11.89 | 72.35 | 7.54 | 2.56 | 11.71 | δ 5.0–9.0 7H  δ 0.5–4.5 34H |

*Chromene compound No. (Example No.) denotes chromene compound No. obtained from the naphthol compound of each Example.

Effect of the Invention

The chromene compound of the present invention develops a color of a neutral tint and has little initial coloration, high color development sensitivity, high color optical density, high double peak characteristic and high fading speed even when it is dispersed into a solution Of a polymer solid matrix as well as excellent durability.

Therefore, a photochromic lens manufactured by using the chromene compound of the present invention exhibits such excellent photochromic properties that it develops a deep color of a neutral tint swiftly when it moves outside and fades to return to its original color swiftly when it returns inside from outside and further has high durability so that it can be used for a long time. Since it has high color development sensitivity, it can develop a color even in a car.

The invention claimed is:

1. A chromene compound having a skeleton represented by the following formula (1):

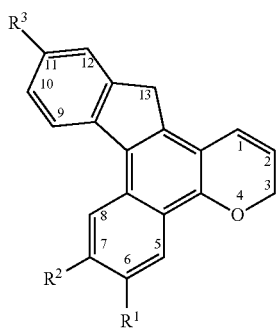

(1)

wherein $R^3$ is a sulfur-containing substituent selected from the group consisting of thiol group, alkylthio group, alkoxyalkylthio group, haloalkylthio group, cycloalkylthio group, arylthio group, heteroarylthio group, alkylsulfonyl group, alkoxyalkylsulfonyl group, haloalkylsulfonyl group cycloalkylsulfonyl group, arylsulfonyl group, heteroarylsulfonyl group, hydroxysulfonyl group, alkylsulfinyl group, alkoxyalkylsulfinyl group, haloalkylsulfinyl group, cycloalkylsulfinyl group, arylsulfinyl group, heteroarylsulfinyl group and hydroxysulfinyl group, and a combination of $R^1$ and $R^2$ is selected from the following (i) to (v):

(i) $R^1$ is an aryl group or a heteroaryl group, and $R^2$ is an electron donating group having a Hammett constant $\sigma_p$ of −0.1 or less;

(ii) $R^1$ is an electron donating group having a Hammett constant $\sigma_p$ of −0.1 or less, and $R^2$ is an aryl group or a heteroaryl group;

(iii) $R^1$ and $R^2$ are each a sulfur-containing substituent selected from the group consisting of thiol group, alkylthio group, alkoxyalkylthio group, haloalkylthio group, cycloalkylthio group, arylthio group and heteroarylthio group;

(iv) $R^1$ is the sulfur-containing substituent, and $R^2$ is a hydrogen atom, hydroxyl group, alkyl group, haloalkyl group, cycloalkyl group, alkoxy group, amino group, heterocyclic group having a ring member nitrogen atom and bonded to a 7-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group; and (v) $R^1$ is a hydrogen atom, hydroxyl group, alkyl group, haloalkyl group, cycloalkyl group, alkoxy group, amino group, aliphatic heterocyclic group having a ring member nitrogen atom and bonded to a 6-position carbon atom via the nitrogen atom, cyano group, nitro group, formyl group, hydroxycarbonyl group, alkylcarbonyl group, alkoxycarbonyl group, halogen atom, aralkyl group, aralkoxy group or aryloxy group, and $R^2$ is the sulfur-containing substituent.

2. The chromene compound according to claim 1 which is represented by the following formula (2):

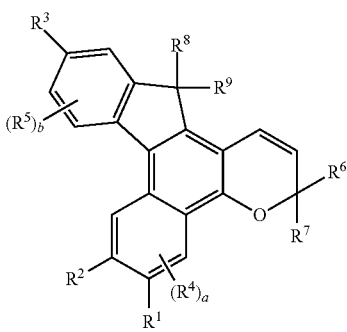

(2)

wherein $R^1$, $R^2$ and $R^3$ are as defined in the above formula (1), $R^4$ and $R^5$ are each independently a hydroxyl group, alkyl group, haloalkyl group, cycloalkyl group, alkoxy group, amino group, heterocyclic group having a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryl group or aryloxy group, $R^6$ and $R^7$ are each independently a group represented by the following formula (3):

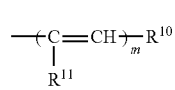
(3)

$R^{10}$ is an aryl group or a heteroaryl group, $R^{11}$ is a hydrogen atom, alkyl group or halogen atom, and "m" is an integer of 1 to 3, group represented by the following formula (4):

(4)

$R^{12}$ is an aryl group or a heteroaryl group, and "n" is an integer of 1 to 3, aryl group, heteroaryl group or alkyl group, $R^6$ and $R^7$ may be bonded together to form an aliphatic hydrocarbon ring together with a carbon atom bonded thereto, $R^8$ and $R^9$ are each independently a hydrogen atom, hydroxyl group, alkyl group, haloalkyl group, cycloalkyl group, alkoxy group, amino group, heterocyclic group having a ring member nitrogen atom and bonded to a 13-position carbon atom via the nitrogen atom, cyano group, nitro group, formyl group, hydroxycarbonyl group, alkylcarbonyl group, alkoxycarbonyl group, halogen atom, aralkyl group, aralkoxy group, aryl group or aryloxy group, and $R^8$ and $R^9$ may be bonded together to form an aliphatic ring having 3 to 20 ring member carbon atoms, condensed polycyclic ring having an aromatic ring or aromatic hetero ring condensed to the aliphatic ring, hetero ring having 3 to 20 ring member atoms, or condensed polycyclic ring having an aromatic ring or an aromatic hetero ring condensed to the hetero ring, "a" is an integer of 0 to 2, "b" is an integer of 0 to 3, and when "a" is 2, two $R^4$'s may be the same or different, and when "b" is 2 or 3, a plurality of $R^5$'s may be the same or different.

3. The chromene compound according to claim 2 which is represented by the following formula (2iv):

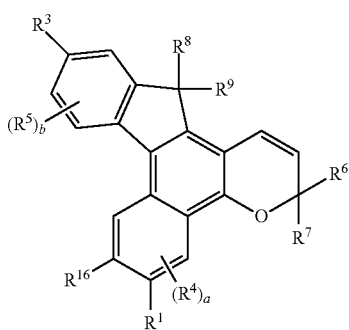
(2iv)

wherein $R^3$, $R^4$, $R^5$, $R^6$, $R^7$, $R^8$, $R^9$, "a" and "b" are as defined in the above formula (2), $R^1$ is defined the same as $R^1$ of the combination (iv) in the above formula (1), and $R^{16}$ is an electron donating group having a Hammett constant $\sigma_p$ of $-0.50$ to $-0.01$ defined as $R^2$ of the combination (iv) in the above formula (1).

4. A photochromic curable composition comprising the chromene compound of claim 3 and a polymerizable monomer.

5. The chromene compound according to claim 2 which is represented by the following formula (2v):

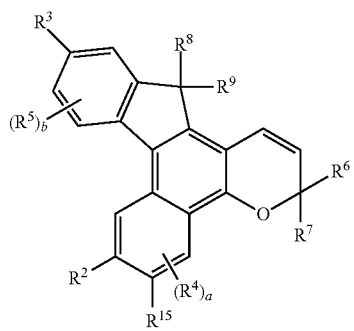
(2v)

wherein $R^3$, $R^4$, $R^5$, $R^6$, $R^7$, $R^8$, $R^9$, "a" and "b" are as defined in the above formula (2), $R^2$ is defined the same as $R^2$ of the combination (v) in the above formula (1), and $R^{15}$ is an electron donating group having a Hammett constant $\sigma_p$ of $-0.50$ to $-0.01$ defined as $R^1$ of the combination (v) in the above formula (1).

6. The chromene compound according to claim 2, wherein $R^8$ and $R^9$ are bonded together to form an aliphatic hydrocarbon ring together with the 13-position carbon atom, and the aliphatic hydrocarbon ring has 3 to 20 ring member carbon atoms and may have at least one substituent selected from the group consisting of alkyl group, haloalkyl group, cycloalkyl group, alkoxy group, amino group, aralkyl group, aryl group and halogen atom.

7. The chromene compound according to claim 6, wherein the aliphatic hydrocarbon ring is a cyclohexane ring substituted by an alkyl group having 1 to 4 carbon atoms.

8. The chromene compound according to claim 2, wherein $R^1$ is an aryl group having 6 to 14 carbon atoms or an aryl group having 6 to 14 carbon atoms and substituted by at least one substituent selected from the group consisting of hydroxyl group, alkyl group, haloalkyl group, cycloalkyl group, alkoxy group, amino group, heterocyclic group having a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aryl group or aryloxy group, and $R^2$ is an electron donating group having a Hammett constant $\sigma_p$ of $-0.1$ or less.

9. The chromene compound according to claim 2, wherein $R^1$ is an aryl group or a heteroaryl group, and $R^2$ is an electron donating group having a Hammett constant $\sigma_p$ of $-0.1$ or less selected from the group consisting of hydroxyl group, alkyl group, cycloalkyl group, alkoxy group, aryloxy group, amino group and heterocyclic group having a ring member nitrogen atom and bonded to the 7-position carbon atom via the nitrogen atom.

10. The chromene compound according to claim 2 which has a ratio $(A_Y/A_B)$ of color optical density having a maximum absorption wavelength at 430 to 530 nm ($A_Y$: value of $\lambda_{max}$) to color optical density having a maximum absorption wavelength at 550 to 650 nm ($A_B$: value of $\lambda_{max}$) of 0.8 to 2.0.

11. A photochromic curable composition comprising the chromene compound of claim 2 and a polymerizable monomer.

12. The chromene compound according to claim 1, wherein $R^1$ is an aryl group having 6 to 14 carbon atoms or an aryl group having 6 to 14 carbon atoms and substituted by at least one substituent selected from the group consisting of hydroxyl group, alkyl group, haloalkyl group, cycloalkyl group, alkoxy group, amino group, heterocyclic group having a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aryl group or aryloxy group, and $R^2$ is an electron donating group having a Hammett constant $\sigma_p$ of −0.1 or less.

13. A photochromic curable composition comprising the chromene compound of claim 12 and a polymerizable monomer.

14. The chromene compound according to claim 1, wherein $R^1$ is an aryl group or a heteroaryl group, and $R^2$ is an electron donating group having a Hammett constant $\sigma_p$ of −0.1 or less selected from the group consisting of hydroxyl group, alkyl group, cycloalkyl group, alkoxy group, aryloxy group, amino group and heterocyclic group having a ring member nitrogen atom and bonded to the 7-position carbon atom via the nitrogen atom.

15. A photochromic curable composition comprising the chromene compound of claim 14 and a polymerizable monomer.

16. The chromene compound according to claim 1 which has a ratio ($A_Y/A_B$) of color optical density having a maximum absorption wavelength at 430 to 530 nm ($A_Y$: value of $\lambda_{max}$) to color optical density having a maximum absorption wavelength at 550 to 650 nm ($A_B$: value of $\lambda_{max}$) of 0.8 to 2.0.

17. A photochromic curable composition comprising the chromene compound of claim 1 and a polymerizable monomer.

18. A photochromic optical article having a polymer molded product containing the chromene compound of claim 1 dispersed therein as a constituent member.

19. An optical article having an optical substrate all or part of at least one surface of which is covered with a polymer film containing the chromene compound of claim 1 dispersed therein as a constituent member.

* * * * *